United States Patent [19]

Chishti et al.

[11] Patent Number: 5,975,893
[45] Date of Patent: Nov. 2, 1999

[54] METHOD AND SYSTEM FOR INCREMENTALLY MOVING TEETH

[75] Inventors: Muhammad Chishti, Menlo Park; Apostolos Lerios, Stanford; Brian Freyburger, Palo Alto; Kelsey Wirth, Menlo Park; Richard Ridgley, Los Altos, all of Calif.

[73] Assignee: Align Technology, Inc., Sunnyvale, Calif.

[21] Appl. No.: 08/947,080

[22] Filed: Oct. 8, 1997

Related U.S. Application Data

[60] Provisional application No. 60/050,342, Jun. 20, 1997.

[51] Int. Cl.$^6$ ..................................................... A61C 3/00
[52] U.S. Cl. .................................................. 433/6; 433/24
[58] Field of Search .................................. 433/6, 18, 20, 433/24

[56] References Cited

U.S. PATENT DOCUMENTS

| | | | |
|---|---|---|---|
| 3,660,900 | 5/1972 | Andrews . | |
| 3,860,803 | 1/1975 | Levine | 235/151.1 |
| 4,504,225 | 3/1985 | Yoshii | 433/6 |
| 4,505,673 | 3/1985 | Yoshii | 433/6 |
| 4,755,139 | 7/1988 | Abbatte et al. | 433/6 |
| 4,798,534 | 1/1989 | Breads | 433/6 |
| 4,856,991 | 8/1989 | Breads et al. | 433/6 |
| 4,936,862 | 6/1990 | Walker et al. | 623/23 |
| 5,011,405 | 4/1991 | Lemchen | 433/24 |
| 5,017,133 | 5/1991 | Miura | 433/20 |
| 5,035,613 | 7/1991 | Breads et al. | 433/6 |
| 5,055,039 | 10/1991 | Abatte et al. | 433/24 |
| 5,059,118 | 10/1991 | Breads et al. | 433/6 |
| 5,139,419 | 8/1992 | Andreiko et al. | 433/24 |
| 5,186,623 | 2/1993 | Breads et al. | 433/6 |
| 5,273,429 | 12/1993 | Rekow et al. | 433/215 |
| 5,338,198 | 8/1994 | Wu et al. | 433/213 |
| 5,340,309 | 8/1994 | Robertson | 433/69 |
| 5,342,202 | 8/1994 | Deshayes | 434/270 |
| 5,367,478 | 11/1994 | Andreiko et al. | 433/24 |
| 5,382,164 | 1/1995 | Stern | 433/223 |
| 5,395,238 | 3/1995 | Andreiko et al. | 433/24 |

(List continued on next page.)

FOREIGN PATENT DOCUMENTS

| | | |
|---|---|---|
| 2369828 | 6/1978 | France . |
| WO 94/10935 | 5/1994 | WIPO . |

OTHER PUBLICATIONS

Biostar Operation & Training Manual, Great Lakes Orthodontics, Ltd. 199 Fire Tower Drive, Tonawanda, New York, 14150–5890, 20 pages total.

Chiappone, "Constructing the gnathologic setup and positioner" *J. Clin. Orthod.* (1980) 14:121–133.

Cottingham, "Gnathologic clear plastic positioner" *Am. J. Orthod.* (1969) 55:23–31.

Cureton, "Correcting malaligned mandibular incisors with removable retainers" *J. Clin. Orthod.* (1996) 30:390–395.

Elsasser, "Some observations on the history and uses of the Kesling positioner" *Am. J. Orthod.* (1950) 36:368–374.

Kamada et al., "Case reports on tooth positioners using LTV vinyl silicone rubber" *J. Nihon University School of Dentistry* (1984) 26(1):11–29.

(List continued on next page.)

*Primary Examiner*—John J. Wilson
*Attorney, Agent, or Firm*—Townsend and Townsend and Crew LLP

[57] ABSTRACT

A system for repositioning teeth comprises a plurality of individual appliances. The appliances are configured to be placed successively on the patient's teeth and to incrementally reposition the teeth from an initial tooth arrangement, through a plurality of intermediate tooth arrangements, and to a final tooth arrangement. The system of appliances is usually configured at the outset of treatment so that the patient may progress through treatment without the need to have the treating professional perform each successive step in the procedure.

29 Claims, 9 Drawing Sheets

U.S. PATENT DOCUMENTS

| | | | |
|---|---|---|---|
| 5,431,562 | 7/1995 | Andreiko et al. | 433/24 |
| 5,447,432 | 9/1995 | Andreiko et al. | 433/24 |
| 5,452,219 | 9/1995 | Dehoff et al. | 364/474.05 |
| 5,454,717 | 10/1995 | Andreiko et al. | 433/24 |
| 5,456,600 | 10/1995 | Andreiko et al. | 433/24 |
| 5,474,448 | 12/1995 | Andreiko et al. | 433/24 |
| 5,533,895 | 7/1996 | Andreiko et al. | 433/24 |
| 5,542,842 | 8/1996 | Andreiko et al. | 433/3 |
| 5,549,476 | 8/1996 | Stern | 433/223 |
| 5,587,912 | 12/1996 | Andersson et al. | 364/468.04 |
| 5,605,459 | 2/1997 | Kuroda et al. | 433/214 |
| 5,607,305 | 3/1997 | Andersson et al. | 433/223 |
| 5,645,421 | 7/1997 | Slootsky | 433/6 |
| 5,683,243 | 11/1997 | Andreiko et al. | 433/3 |

OTHER PUBLICATIONS

Kamada et al., "Construction of tooth positioners with LTV vinyl silicone rubber and some case reports" *J. Nihon University School of Dentistry* (1982) 24(1):1–27.

Kesling, "The philosophy of the tooth positioning appliance" *Am. J. Orthod. Oral. Surg.* (1945) 31(6):297–304.

Kesling, "Coordinating the predetermined pattern and tooth positioner with conventional treatment" *Am. J. Orthod. Oral. Surg.* (1946) 32:285–293.

Kleemann et al., "The speed positioner" *J. Clin. Orthod.* (1996) 30:673–680.

Kuroda et al., "Three–dimensional dental cast analyzing system using laser scanning" *Am. J. Orthod. Dentofac. Orthop.* (1996) 110:365–369.

Nishiyama et al., "A new construction of tooth repositioner by LTV vinyl silicone rubber" *J. Nihon University School of Dentistry* (1977) 19(2):93–102.

*Nippon Dental Review* "New orthodontic device–dynamic positioner (.D.P.)–I. Approach to the proposal of D.P. and transparent silicone rubber" (1980) 452:61–74.

*Nippon Dental Review* "New orthodontic device–dynamic positioner (D.P.)–II. Pratical application and construction of D.P." (1980) 454:107–130.

*Nippon Dental Review* "New orthodontic device–dynamic positioner (D.P.)–III. Case reports of reversed occlusion" (1980) 457:146–164.

*Nippon Dental Review* "New orthodontic device–dynamic positioner (D.P.)–Case reports of reversed occlusion" (1980) 458:112–129.

*Raintree Essix™ & ARS Materials, Inc.*, Raintree Essix™ Technical Magazine Table of Contents and Essix™ Applications, http://www.essix.com/magazine/default.html (Aug. 13, 1997) 7 pages total.

Shilliday, "Minimizing finishing problems with the mini–positioner" *Am. J. Orthod.* (1971) 59:596–599.

Warunek et al., "Clinical use of silicone elastomer appliances" *JCO* (1989) XXIII(10):694–700.

Warunek et al., "Physical and mechanical properties of elastomers in orthodontic positioners" *Am. J. Orthod. Dentofac. Orthop.* (1989) 95:388–400.

Wells, "Application of the positioner appliance in orhodontic treatment" *Am. J. Orthodont.* (1970) 58:351–366.

METHOD AND SYSTEM FOR INCREMENTALLY MOVING TEETH

The present application is a continuation-in-part of provisional Application Ser. No. 60/050,342; filed on Jun. 20, 1997, the full disclosure of which is incorporated herein by reference.

BACKGROUND OF THE INVENTION

1. Field of the Invention

The present invention is related generally to the field of orthodontics. More particularly, the present invention is related to a method and system for incrementally moving teeth from an initial tooth arrangement to a final tooth arrangement.

Repositioning teeth for aesthetic or other reasons is accomplished conventionally by wearing what are commonly referred to as "braces." Braces comprise a variety of appliances such as brackets, archwires, ligatures, and O-rings. Attaching the appliances to a patient's teeth is a tedious and time consuming enterprise requiring many meetings with the treating orthodontist. Consequently, conventional orthodontic treatment limits an orthodontist's patient capacity and makes orthodontic treatment quite expensive.

Before fastening braces to a patient's teeth, at least one appointment is typically scheduled with the orthodontist, dentist, and/or X-ray laboratory so that X-rays and photographs of the patient's teeth and jaw structure can be taken. Also during this preliminary meeting, or possibly at a later meeting, an alginate mold of the patient's teeth is typically made. This mold provides a model of the patient's teeth that the orthodontist uses in conjunction with the X-rays and photographs to formulate a treatment strategy. The orthodontist then typically schedules one or more appointments during which braces will be attached to the patient's teeth.

At the meeting during which braces are first attached, the teeth surfaces are initially treated with a weak acid. The acid optimizes the adhesion properties of the teeth surfaces for brackets and bands that are to be bonded to them. The brackets and bands serve as anchors for other appliances to be added later. After the acid step, the brackets and bands are cemented to the patient's teeth using a suitable bonding material. No force-inducing appliances are added until the cement is set. For this reason, it is common for the orthodontist to schedule a later appointment to ensure that the brackets and bands are well bonded to the teeth.

The primary force-inducing appliance in a conventional set of braces is the archwire. The archwire is resilient and is attached to the brackets by way of slots in the brackets. The archwire links the brackets together and exerts forces on them to move the teeth over time. Twisted wires or elastomeric O-rings are commonly used to reinforce attachment of the archwire to the brackets. Attachment of the archwire to the brackets is known in the art of orthodontia as "ligation" and wires used in this procedure are called "ligatures." The elastomeric O-rings are called "plastics."

After the archwire is in place, periodic meetings with the orthodontist are required, during which the patient's braces will be adjusted by installing a different archwire having different force-inducing properties or by replacing or tightening existing ligatures. Typically, these meetings are scheduled every three to six weeks.

As the above illustrates, the use of conventional braces is a tedious and time consuming process and requires many visits to the orthodontist's office. Moreover, from the patient's perspective, the use of braces is unsightly, uncomfortable, presents a risk of infection, and makes brushing, flossing, arid other dental hygiene procedures difficult.

For these reasons, it would be desirable to provide alternative methods arid systems for repositioning teeth. Such methods and systems should be economical, and in particular should reduce the amount of time required by the orthodontist in planning and overseeing each individual patient. The methods and systems should also be more acceptable to the patient, in particular being less visible, less uncomfortable, less prone to infection, and more compatible with daily dental hygiene. At least some of these objectives will be met by the methods and systems of the present invention described hereinafter.

2. Description of the Background Art

Tooth positioners for finishing orthodontic treatment are described by Kesling in the *Am. J. Orthod. Oral. Surg.* 31:297–304 (1945) and 32:285–293 (1946). The use of silicone positioners for the comprehensive orthodontic realignment of a patient's teeth is described in Warunek et al. (1989) *J. Clin. Orthod.* 23:694–700. Clear plastic retainers for finishing and maintaining tooth positions are commercially available from Raintree Essix, Inc., New Orleans, La. 70125, and Tru-Tain Plastics, Rochester, Minn. 55902. The manufacture of orthodontic positioners is described in U.S. Pat. Nos. 5,186,623; 5,059,118; 5,055,039; 5,035,613; 4,856,991; 4,798,534; and 4,755,139.

Other publications describing the fabrication and use of dental positioners include Kleemann and Janssen (1996) *J. Clin. Orthodon.* 30:673–680; Cureton (1996) *J. Clin. Orthodon.* 30:390–395; Chiappone (1980) *J. Clin. Orthodon.* 14:121–133; Shilliday (1971) *Am. J. Orthodontics* 59:596–599; Wells (1970) *Am. J. Orthodontics* 58:351–366; and Cottingham (1969) *Am. J. Orthodontics* 55:23–31.

Kuroda et al. (1996) *Am. J. Orthodontics* 110:365–369 describes a method for laser scanning a plaster dental cast to produce a digital image of the cast. See also U.S. Pat. No. 5,605,459.

U.S. Pat. Nos. 5,533,895; 5,474,448; 5,454,717; 5,447,432; 5,431,562; 5,395,238; 5,368,478; and 5,139,419, assigned to Ormco Corporation, describe methods for manipulating digital images of teeth for designing orthodontic appliances.

U.S. Pat. No. 5,011,405 describes a method for digitally imaging a tooth and determining optimum bracket positioning for orthodontic treatment. Laser scanning of a molded tooth to produce a three-dimensional model is described in U.S. Pat. No. 5,338,198. U.S. Pat. No. 5,452,219 describes a method for laser scanning a tooth model and milling a tooth mold. Digital computer manipulation of tooth contours is described in U.S. Pat. Nos. 5,607,305 and 5,587,912. Computerized digital imaging of the jaw is described in U.S. Pat. Nos. 5,342,202 and 5,340,309. Other patents of interest include U.S. Pat. Nos. 5,549,476; 5,382,164; 5,273,429; 4,936,862; 3,860,803; 3,660,900; 5,645,421; 5,055,039; 4,798,534; 4,856,991; 5,035,613; 5,059,118; 5,186,623; and 4,755,139.

SUMMARY OF THE INVENTION

The present invention provides improved methods and systems for repositioning teeth from an initial tooth arrangement to a final tooth arrangement. Repositioning is accomplished with a system comprising a series of appliances configured to receive the teeth in a cavity and incrementally reposition individual teeth in a series of at least three successive steps, usually including at least four successive steps, often including at least ten steps, sometimes including at least twenty-five steps, and occasionally including forty or more steps. Most often, the methods and systems will reposition teeth in from ten to twenty-five successive steps, although complex cases involving many of the patient's teeth may take forty or more steps. The successive use of a number of such appliances permits each appliance to be configured to move individual teeth in small increments, typically less than 2 mm, preferably less than 1 mm, and more preferably less than 0.5 mm. These limits refer to the maximum linear translation of any point on a tooth as a result of using a single appliance. The movements provided by successive appliances, of course, will usually not be the same for any particular tooth. Thus, one point on a tooth may be moved by a particular distance as a result of the use of one appliance and thereafter moved by a different distance and/or in a different direction by a later appliance.

The individual appliances will preferably comprise a polymeric shell having the teeth-receiving cavity formed therein, typically by molding as described below. Each individual appliance will be configured so that its tooth-receiving cavity has a geometry corresponding to an intermediate or end tooth arrangement intended for that appliance. That is, when an appliance is first worn by the patient, certain of the teeth will be misaligned relative to an undeformed geometry of the appliance cavity. The appliance, however, is sufficiently resilient to accommodate or conform to the misaligned teeth, and will apply sufficient resilient force against such misaligned teeth in order to reposition the teeth to the intermediate or end arrangement desired for that treatment step.

Systems according to the present invention will include at least a first appliance having a geometry selected to reposition a patient's teeth from the initial tooth arrangement to a first intermediate arrangement where individual teeth will be incrementally repositioned. The system will further comprise at least one intermediate appliance having a geometry selective to progressively reposition teeth from the first intermediate arrangement to one or more successive intermediate arrangements. The system will still further comprise a final appliance having a geometry selected to progressively reposition teeth from the last intermediate arrangement to the desired final tooth arrangement. In some cases, it will be desirable to form the final appliance or several appliances to "over correct" the final tooth position, as discussed in more detail below.

As will be described in more detail below in connection with the methods of the present invention, the systems may be planned and all individual appliances fabricated at the outset of treatment, and the appliances may thus be provided to the patient as a single package or system. The order in which the appliances are to be used will be clearly marked, (e.g. by sequential numbering) so that the patient can place the appliances over his or her teeth at a frequency prescribed by the orthodontist or other treating professional. Unlike braces, the patient need not visit the treating professional every time an adjustment in the treatment is made. While the patients will usually want to visit their treating professionals periodically to assure that treatment is going according to the original plan, eliminating the need to visit the treating professional each time an adjustment is to be made allows the treatment to be carried out in many more, but smaller, successive steps while still reducing the time spent by the treating professional with the individual patient. Moreover, the ability to use polymeric shell appliances which are more comfortable, less visible, and removable by the patient, greatly improves patient compliance, comfort, and satisfaction.

According to a method of the present invention, a patient's teeth are repositioned from an initial tooth arrangement to a final tooth arrangement by placing a series of incremental position adjustment appliances in the patient's mouth. Conveniently, the appliances are not affixed and the patient may place and replace the appliances at any time during the procedure. The first appliance of the series will have a geometry selected to reposition the teeth from the initial tooth arrangement to a first intermediate arrangement. After the first intermediate arrangement is approached or achieved, one or more additional (intermediate) appliances will be successively placed on the teeth, where such additional appliances have geometries selected to progressively reposition teeth from the first intermediate arrangement through successive intermediate arrangement(s). The treatment will be finished by placing a final appliance in the patient's mouth, where the final appliance has a geometry selected to progressively reposition teeth from the last intermediate arrangement to the final tooth arrangement. The final appliance or several appliances in the series may have a geometry or geometries selected to over correct the tooth arrangement, i.e. have a geometry which would (if fully achieved) move individual teeth beyond the tooth arrangement which has been selected as the "final." Such over correction may be desirable in order to offset potential relapse after the repositioning method has been terminated, i.e. to permit some movement of individual teeth back toward their precorrected positions. Over correction may also be beneficial to speed the rate of correction, i.e. by having an appliance with a geometry that is positioned beyond a desired intermediate or final position, the individual teeth will be shifted toward the position at a greater rate. In such cases, treatment can be terminated before the teeth reach the positions defined by the final appliance or appliances. The method will usually comprise placing at least two additional appliances, often comprising placing at least ten additional appliances, sometimes placing at least twenty-five additional appliances, and occasionally placing at least forty or more additional appliances. Successive appliances will be replaced when the teeth either approach (within a preselected tolerance) or have reached the target end arrangement for that stage of treatment, typically being replaced at an interval in the range from 2 days to 20 days, usually at an interval in the range from 5 days to 10 days.

Often, it may be desirable to replace the appliances at a time before the "end" tooth arrangement of that treatment stage is actually achieved. It will be appreciated that as the teeth are gradually repositioned and approach the geometry defined by a particular appliance, the repositioning force on the individual teeth will diminish greatly. Thus, it may be possible to reduce the overall treatment time by replacing an earlier appliance with the successive appliance at a time when the teeth have been only partially repositioned by the earlier appliance. Thus, the FDDS can actually represent an over correction of the final tooth position. This both speeds the treatment and can offset patient relapse.

In general, the transition to the next appliance can be based on a number of factors. Most simply, the appliances can be replaced on a predetermined schedule or at a fixed time interval (i.e. number of days for each appliance) determined at the outset based on an expected or typical patient response. Alternatively, actual patient response can be taken into account, e.g. a patient can advance to the next appliance when that patient no longer perceives pressure on their teeth from a current appliance, i.e. the appliance they have been wearing fits easily over the patient's teeth and the patient experiences little or no pressure or discomfort on his or her teeth. In some cases, for patients whose teeth are responding very quickly, it may be possible for a treating professional to decide to skip one or more intermediate appliances, i.e. reduce the total number of appliances being used below the number determined at the outset. In this way, the overall treatment time for a particular patient can be reduced.

In another aspect, methods of the present invention comprise repositioning teeth using appliances comprising polymeric shells having cavities shaped to receive and resiliently reposition teeth to produce a final tooth arrangement. The present invention provides improvements to such methods which comprise determining at the outset of treatment geometries for at least three of the appliances which are to be worn successively by a patient to reposition teeth from an initial tooth arrangement to the final tooth arrangement. Preferably, at least four geometries will be determined in the outset, often at least ten geometries, frequently at least twenty-five geometries, and sometimes forty or more geometries. Usually, the tooth positions defined by the cavities in each successive geometry differ from those defined by the prior geometry by no more than 2 mm, preferably no more than 1 mm, and often no more than 0.5 mm, as defined above.

In yet another aspect, methods are provided for producing a digital data set representing a final tooth arrangement. The methods comprise providing an initial data set representing an initial tooth arrangement, and presenting a visual image based on the initial data set. The visual image is then manipulated to reposition individual teeth in the visual image. A final digital data set is then produced which represents the final tooth arrangement with repositioned teeth as observed in the visual image. Conveniently, the initial digital data set may be provided by conventional techniques, including digitizing X-ray images, images produced by computer-aided tomography (CAT scans), images produced by magnetic resonance imaging (MRI), and the like. Preferably, the images will be three-dimensional images and digitization may be accomplished using conventional technology. Usually, the initial digital data set is provided by producing a plaster cast of the patient's teeth (prior to treatment) by conventional techniques. The plaster cast so produced may then be scanned using laser or other scanning equipment to produce a high resolution digital representation of the plaster cast of the patient's teeth. Use of the plaster cast is preferred since it does not expose the patient to X-rays or subject the patient to the inconvenience of an MRI scan.

Once the digital data set is acquired, an image can be presented and manipulated on a suitable computer system equipped with computer-aided design software, as described in greater detail below. The image manipulation will usually comprise defining boundaries about at least some of the individual teeth, and causing the images of the teeth to be moved relative to the jaw and other teeth by manipulation of the image via the computer. The image manipulation can be done entirely subjectively, i.e. the user may simply reposition teeth in an aesthetically and/or therapeutically desired manner based on observation of the image alone. Alternatively, the computer system could be provided with rules and algorithms which assist the user in repositioning the teeth. In some instances, it will be possible to provide rules and algorithms which reposition the teeth in a fully automatic manner, i.e. without user intervention. Once the individual teeth have been repositioned, a final digital data set representing the desired final tooth arrangement will be generated and stored.

A preferred method for determining the final tooth arrangement is for the treating professional to define the final tooth positions, e.g. by writing a prescription. The use of prescriptions for defining the desired outcomes of orthodontic procedures is well known in the art. When a prescription or other final designation is provided, the image can then be manipulated to match the prescription. In some cases, it would be possible to provide software which could interpret the prescription in order to generate the final image and thus the digital data set representing the final tooth arrangement.

In yet another aspect, methods according to the present invention are provided for producing a plurality of digital data sets representing a series of discrete tooth arrangements progressing from an initial tooth arrangement to a final tooth arrangement. Such methods comprise providing a digital data set representing an initial tooth arrangement (which may be accomplished according to any of the techniques set forth above). A digital data set representing a final tooth arrangement is also provided. Such final digital data set may be determined by the methods described previously. The plurality of successive digital data sets are then produced based on the initial digital data set and the final digital data set. Usually, the successive digital data sets are produced by determining positional differences between selected individual teeth in the initial data set and in the final data set and interpolating said differences. Such interpolation may be performed over as many discrete stages as may be desired, usually at least three, often at least four, more often at least ten, sometimes at least twenty-five, and occasionally forty or more. Many times, the interpolation will be linear interpolation for some or all of the positional differences. Alternatively, the interpolation may be nonlinear. The positional differences will correspond to tooth movements where the maximum linear movement of any point on a tooth is 2 mm or less, usually being 1 mm or less, and often being 0.5 mm or less.

Often, the user will specify certain target intermediate tooth arrangements, referred to as "key frames," which are incorporated directly into the intermediate digital data sets. The methods of the present invention then determine successive digital data sets between the key frames in the manner described above, e.g. by linear or non-linear interpolation between the key frames. The key frames may be determined by a user, e.g. the individual manipulating a visual image at the computer used for generating the digital data sets, or alternatively may be provided by the treating professional as a prescription in the same manner as the prescription for the final tooth arrangement.

In still another aspect, methods according to the present invention provide for fabricating a plurality of dental incremental position adjustment appliances. Said methods comprise providing an initial digital data set, a final digital data set, and producing a plurality of successive digital data sets representing the target successive tooth arrangements, generally as just described. The dental appliances are then fabricated based on at least some of the digital data sets representing the successive tooth arrangements. Preferably, the fabricating step comprises controlling a fabrication machine based on the successive digital data sets to produce successive positive models of the desired tooth arrangements. The dental appliances are then produced as negatives of the positive models using conventional positive pressure or vacuum fabrication techniques. The fabrication machine may comprise a stereolithography or other similar machine which relies on selectively hardening a volume of non-hardened polymeric resin by scanning a laser to selectively harden the resin in a shape based on the digital data set. Other fabrication machines which could be utilized in the methods of the present invention include tooling machines and wax deposition machines.

In still another aspect, methods of the present invention for fabricating a dental appliance comprise providing a digital data set representing a modified tooth arrangement for a patient. A fabrication machine is then used to produce a positive model of the modified tooth arrangement based on the digital data set. The dental appliance is then produced as a negative of the positive model. The fabrication machine may be a stereolithography or other machine as described above, and the positive model is produced by conventional pressure or vacuum molding techniques.

In a still further aspect, methods for fabricating a dental appliance according to the present invention comprise providing a first digital data set representing a modified tooth arrangement for a patient. A second digital data set is then produced from the first digital data set, where the second data set represents a negative model of the modified tooth arrangement. The fabrication machine is then controlled based on the second digital data set to produce the dental appliance. The fabrication machine will usually rely on selectively hardening a non-hardened resin to produce the appliance. The appliance typically comprises a polymeric shell having a cavity shape to receive and resiliently reposition teeth from an initial tooth arrangement to the modified tooth arrangement.

DESCRIPTION OF THE SPECIFIC EMBODIMENTS

According to the present invention, systems and methods are provided for incrementally moving teeth using a plurality of discrete appliances, where each appliance successively moves one or more of the patient's teeth by relatively small amounts. The tooth movements will be those normally associated with orthodontic treatment, including translation in all three orthogonal directions relative to a vertical centerline, rotation of the tooth centerline in the two orthodontic directions ("root angulation" and "torque"), as well as rotation about the centerline.

Figure 1A:
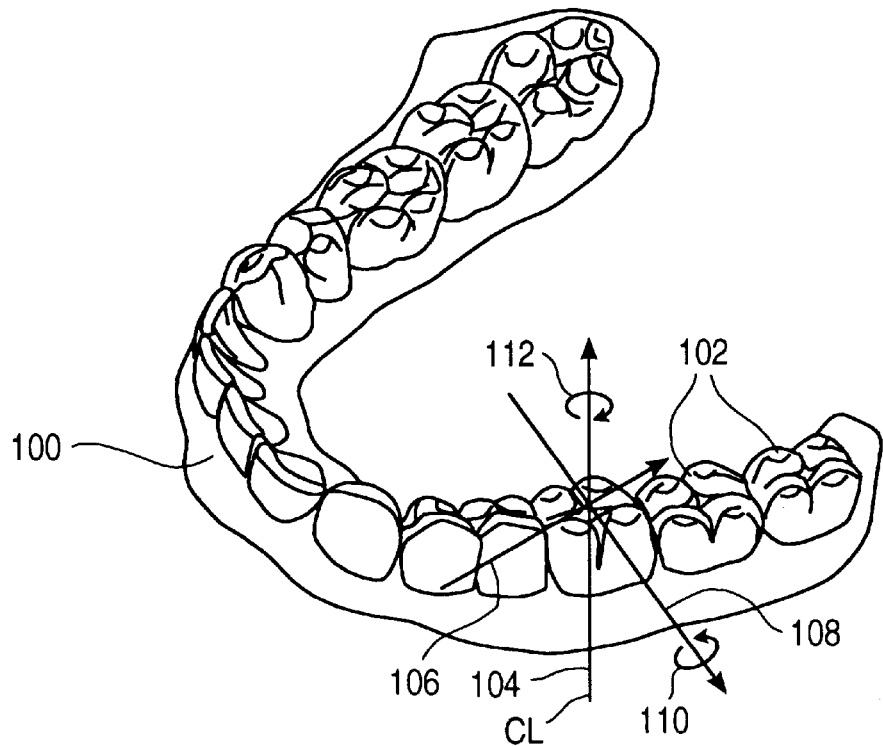
FIG. 1A illustrates a patient's jaw and provides a general indication of how teeth may be moved by the methods and apparatus of the present invention.
Figure 1B:
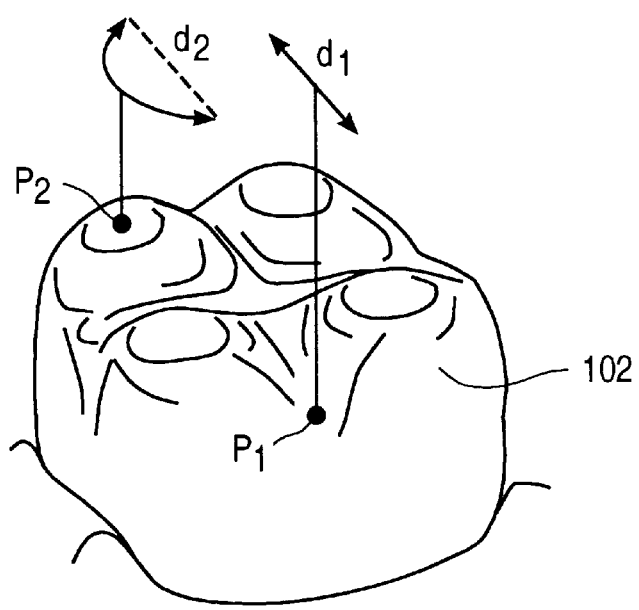
FIG. 1B illustrates a single tooth from FIG. 1A and defines how tooth movement distances are determined.

Referring now to FIG. 1A, a representative jaw 100 includes sixteen teeth 102. The present invention is intended to move at least some of these teeth from an initial tooth arrangement to a final tooth arrangement. To understand how the teeth may be moved, an arbitrary centerline (CL) is drawn through one of the teeth 102. With reference to this centerline (CL), the teeth may be moved in the orthogonal directions represented by axes 104, 106, and 108 (where 104 is the centerline). The centerline may be rotated about the axis 108 (root angulation) and 104 (torque) as indicated by arrows 110 and 112, respectively. Additionally, the tooth may be rotated about the centerline, as represented by arrow 114. Thus, all possible free-form motions of the tooth can be performed. Referring now to FIG. 1B, the magnitude of any tooth movement achieved by the methods and devices of the present invention will be defined in terms of the maximum linear translation of any point P on a tooth 102. Each point $P_i$ will undergo a cumulative translation as that tooth is moved in any of the orthogonal or rotational directions defined in FIG. 1A. That is, while the point will usually follow a non-linear path, there will be a linear distance between any point in the tooth when determined at any two times during the treatment. Thus, an arbitrary point $P_1$ may in fact undergo a true side-to-side translation as indicated by arrow $d_1$, while a second arbitrary point $P_2$ may travel along an arcuate path, resulting in a final translation $d_2$. Many aspects of the present invention are defined in terms of the maximum permissible movement of a point $P_i$ induced by the methods in any particular tooth. Such maximum tooth movement, in turn, is defined as the maximum linear translation of that point $P_i$ on the tooth which undergoes the maximum movement for that tooth in any treatment step.

Figure 1C:
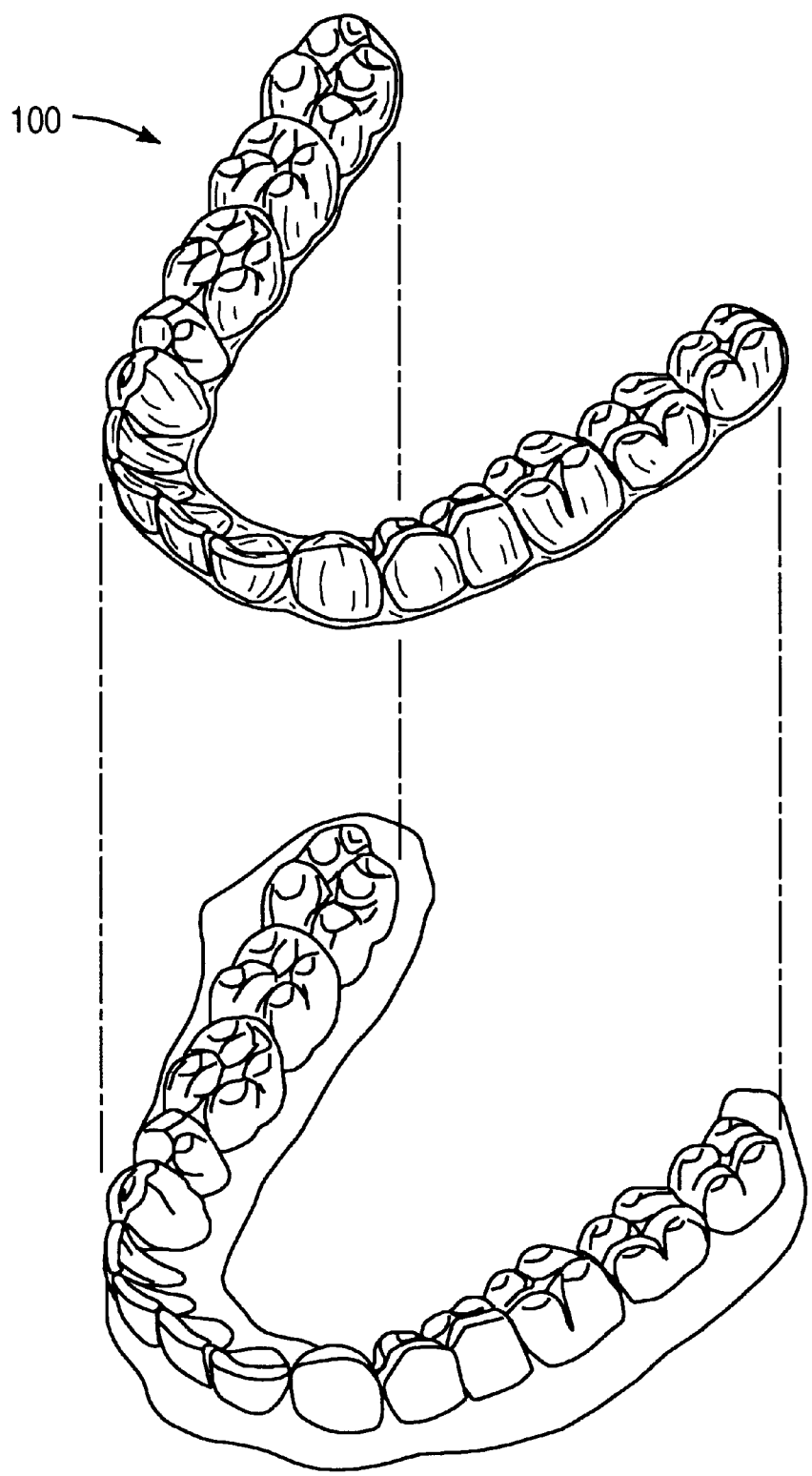
FIG. 1C illustrates the jaw of FIG. 1A together with an incremental position adjustment appliance which has been configured according to the methods of the present invention.

Referring now to FIG. 1C, systems according to the present invention will comprise a plurality of incremental position adjustment appliances. The appliances are intended to effect incremental repositioning of individual teeth in the jaw as described generally above. In a broadest sense, the methods of the present invention can employ any of the known positioners, retainers, or other removable appliances which are known for finishing and maintaining teeth positions in connection with conventional orthodontic treatment. The systems of the present invention, in contrast with prior apparatus and systems, will provide a plurality of such appliances intended to be worn by a patient successively in order to achieve the gradual tooth repositioning as described herein. A preferred appliance 100 will comprise a polymeric shell having a cavity shaped to receive and resiliently reposition teeth from one tooth arrangement to a successive tooth arrangement. The polymeric shell will preferably, but not necessarily, fit over all teeth present in the upper or lower jaw. Often, only certain one(s) of the teeth will be repositioned while others of the teeth will provide a base or anchor region for holding the repositioning appliance in place as it applies the resilient repositioning force against the tooth or teeth to be repositioned. In complex cases, however, many or most of the teeth will be repositioned at some point during the treatment. In such cases, the teeth which are moved can also serve as a base or anchor region for holding the repositioning appliance. Additionally, the gums and/or the palette can serve as an anchor region, thus allowing all or nearly all of the teeth to be repositioned simultaneously.

The polymeric appliance 100 of FIG. 1C is preferably formed from a thin sheet of a suitable elastomeric polymeric, such as Tru-Tain 0.03 in. thermal forming dental material, Tru-Tain Plastics, Rochester, Minn. 55902. Usually, no wires or other means will be provided for holding the appliance in place over the teeth. In some cases, however, it will be desirable or necessary to provide individual anchors on teeth with corresponding receptacles or apertures in the appliance 100 so that the appliance can apply an upward force on the tooth which would not be possible in the absence of such an anchor. Specific methods for producing the appliances 100 are described hereinafter.

Figure 2:
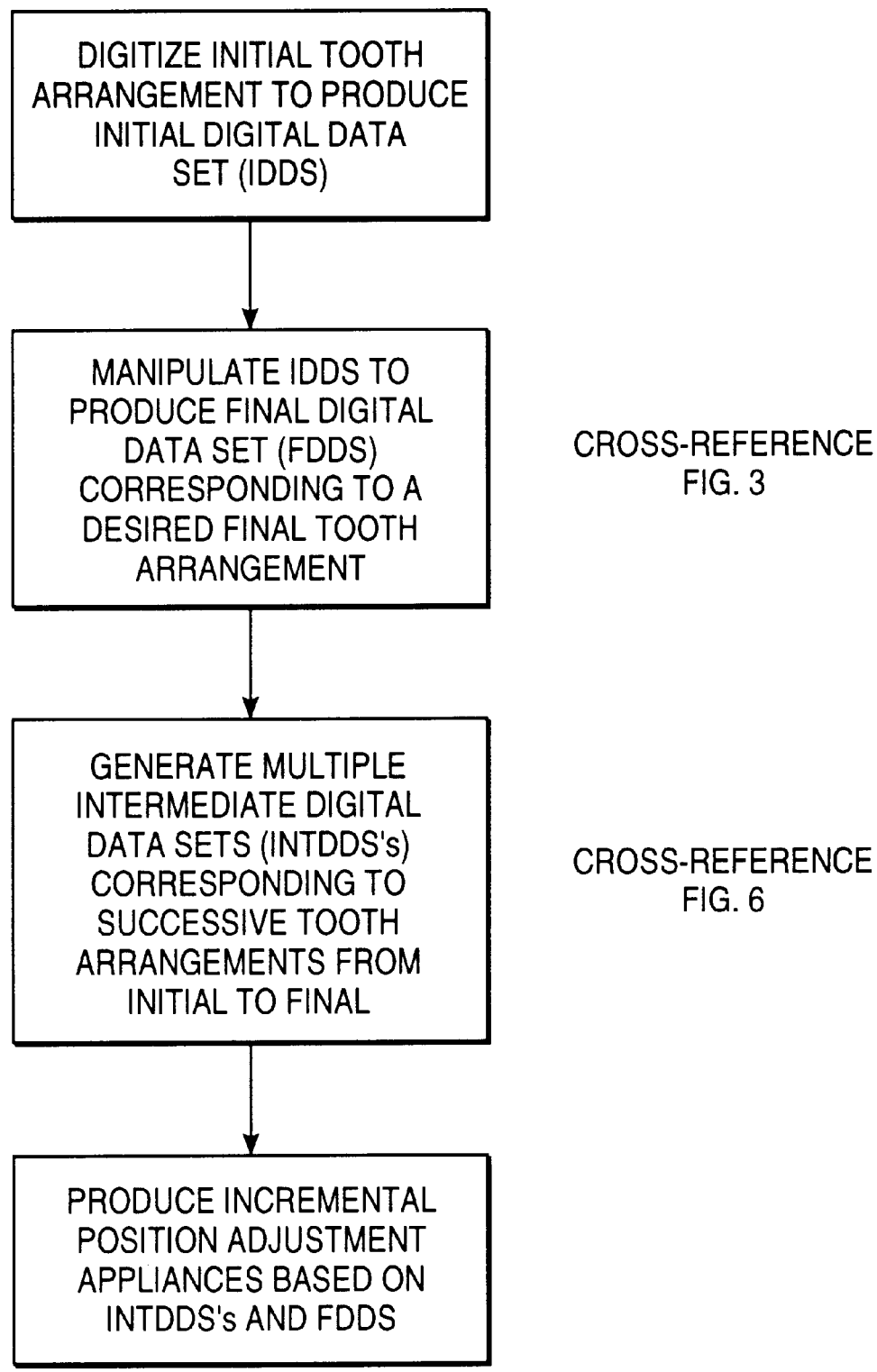
FIG. 2 is a block diagram illustrating the steps of the present invention for producing a system of incremental position adjustment appliances.

Referring now to FIG. 2, the overall method of the present invention for producing the incremental position adjustment appliances for subsequent use by a patient to reposition the patient's teeth will be described. As a first step, a digital data set representing an initial tooth arrangement is obtained, referred to hereinafter as the IDDS. The IDDS may be obtained in a variety of ways. For example, the patient's teeth may be scanned or imaged using well known technology, such as X-rays, three-dimensional x-rays, computer-aided tomographic images or data sets, magnetic resonance images, etc. Methods for digitizing such conventional images to produce data sets useful in the present invention are well known and described in the patent and medical literature. Usually, however, the present invention will rely on first obtaining a plaster cast of the patient's teeth by well known techniques, such as those described in *Graber, Orthodontics: Principle and Practice*, Second Edition, Saunders, Philadelphia, 1969, pp. 401–415. After the tooth casting is obtained, it can be digitally scanned using a conventional laser scanner or other range acquisition system to produce the IDDS. The data set produced by the range acquisition system may, of course, be converted to other formats to be compatible with the software which is used for manipulating images within the data set, as described in more detail below. General techniques for producing plaster casts of teeth and generating digital models using laser scanning techniques are described, for example, in U.S. Pat. No. 5,605,459, the full disclosure of which is incorporated herein by reference.

There are a variety of range acquisition systems, generally categorized by whether the process of acquisition requires contact with the three dimensional object. A contact-type range acquisition system utilizes a probe, having multiple degrees of translational and/or rotational freedom. By recording the physical displacement of the probe as it is drawn across the sample surface, a computer-readable representation of the sample object is made. A non-contact-type range acquisition device can be either a reflective-type or transmissive-type system. There are a variety of reflective systems in use. Some of these reflective systems utilize non-optical incident energy sources such as microwave radar or sonar. Others utilize optical energy. Those non-contact-type systems working by reflected optical energy further contain special instrumentation configured to permit certain measuring techniques to be performed (e.g., imaging radar, triangulation and interferometry).

A preferred range acquisition system is an optical, reflective, non-contact-type scanner. Non-contact-type scanners are preferred because they are inherently nondestructive (i.e., do not damage the sample object), are generally characterized by a higher capture resolution and scan a sample in a relatively short period of time. One such scanner is the Cyberware Model 15 manufactured by Cyberware, Inc., Monterey, Calif.

Either non-contact-type or contact-type scanners may also include a color camera, that when synchronized with the scanning capabilities, provides a means for capturing, in digital format, a color representation of the sample object. The importance of this further ability to capture not just the shape of the sample object but also its color is discussed below.

The methods of the present invention will rely on manipulating the IDDS at a computer or workstation having a suitable graphical user interface (GUI) and software appropriate for viewing and modifying the images. Specific aspects of the software will be described in detail hereinafter. While the methods will rely on computer manipulation of digital data, the systems of the present invention comprising multiple dental appliances having incrementally differing geometries may be produced by non-computer-aided techniques. For example, plaster casts obtained as described above may be cut using knives, saws, or other cutting tools in order to permit repositioning of individual teeth within the casting. The disconnected teeth may then be held in place by soft wax or other malleable material, and a plurality of intermediate tooth arrangements can then be prepared using such a modified plaster casting of the patient's teeth. The different arrangements can be used to prepare sets of multiple appliances, generally as described below, using pressure and vacuum molding techniques. While such manual creation of the appliance systems of the present invention will generally be much less preferred, systems so produced will come within the scope of the present invention.

Referring again to FIG. 2, after the IDDS has been obtained, the digital information will be introduced to the computer or other workstation for manipulation. In the preferred approach, individual teeth and other components will be "cut" to permit their individual repositioning or removal from the digital data. After thus "freeing" the components, the user will often follow a prescription or other written specification provided by the treating professional. Alternatively, the user may reposition them based on the visual appearance or using rules and algorithms programmed into the computer. Once the user is satisfied with the final arrangement, the final tooth arrangement is incorporated into a final digital data set (FDDS).

Based on both the IDDS and the FDDS, a plurality of intermediate digital data sets (INTDDS's) are generated to correspond to successive intermediate tooth arrangements. The system of incremental position adjustment appliances can then be fabricated based on the INTDDS's, as described in more detail below.

Figure 3:
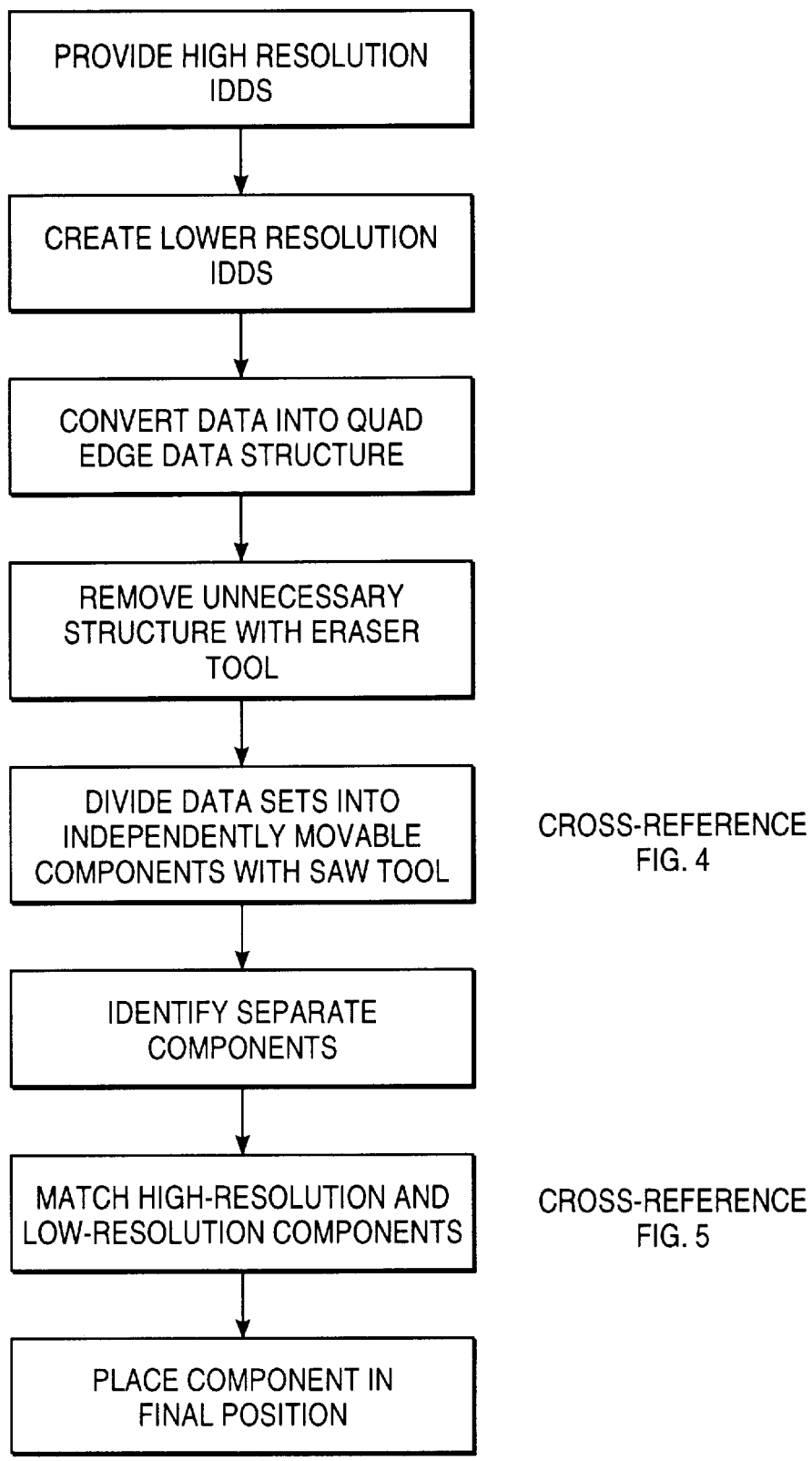
FIG. 3 is a block diagram setting forth the steps for manipulating an initial digital data set representing an initial tooth arrangement to produce a final digital data set corresponding to a desired final tooth arrangement.

FIG. 3 illustrates a representative technique for manipulating the IDDS to produce the FDDS on the computer. Usually, the data from the digital scanner will be in a high resolution form. In order to reduce the computer time necessary to generate images, a parallel set of digital data set representing the IDDS at a lower resolution will be created. The user will manipulate the lower resolution images while the computer will update the high resolution data set as necessary. The user can also view/manipulate the high resolution model if the extra detail provided in that model is useful. The IDDS will also be converted into a quad edge data structure if not already present in that form. A quad edge data structure is a standard topological data structure defined in *Primitives for the Manipulation of General Subdivisions and the Computation of Voronoi Diagrams*, ACM Transactions of Graphics, Vol. 4, No. 2, April 1985, pp. 74–123. Other topological data structures, such as the winged-edge data structure, could also be used.

As an initial step, while viewing the three-dimensional image of the patient's jaw, including the teeth, gingivae, and other oral tissue, the user will usually delete structure which is unnecessary for image manipulation and/or final production of an appliance. These unwanted sections of the model may be removed using an eraser tool to perform a solid modeling subtraction. The tool is represented by a graphic box. The volume to be erased (the dimensions, position, and orientation of the box) are set by the user employing the GUI. Typically, unwanted sections would include extraneous gum area and the base of the originally scanned cast. Another application for this tool is to stimulate the extraction of teeth and the "shaving down" of tooth surfaces. This is necessary when additional space is needed in the jaw for the final positioning of a tooth to be moved. The treating professional may choose to determine which teeth will be shaved and/or which teeth will be extracted. Shaving allows the patient to maintain their teeth when only a small amount of space is needed. Typically, extraction and shaving, of course, will be utilized in the treatment planning only when the actual patient teeth are to be extracted and/or shaved prior to initiating repositioning according to the methods of the present invention.

Removing unwanted and/or unnecessary sections of the model increases data processing speed and enhances the visual display. Unnecessary sections include those not needed for creation of the tooth repositioning appliance. The removal of these unwanted sections reduces the complexity and size of the digital data set, thus accelerating manipulations of the data set and other operations.

After the user positions and sizes the eraser tool and instructs the software to erase the unwanted section, all triangles within the box set by the user will be removed and the border triangles are modified to leave a smooth, linear border. The software deletes all of the triangles within the box and clips all triangles which cross the border of the box. This requires generating new vertices on the border of the box. The holes created in the model at the faces of the box are re-triangulated and closed using the newly created vertices.

The saw tool is used to define the individual teeth (or possibly groups of teeth) to be moved. The tool separates the scanned image into individual graphic components enabling the software to move the tooth or other component images independent of remaining portions of the model. The saw tool defines a path for cutting the graphic image by using two cubic B-spline curves lying in space, possibly constrained to parallel planes. A set of lines connects the two curves and shows the user the general cutting path. The user may edit the control points on the cubic B-splines, the thickness of the saw cut, and the number of erasers used, as described below.

Thickness: When a cut is used to separate a tooth, the user will usually want the cut to be as thin as possible. However, the user may want to make a thicker cut, for example, when shaving down surrounding teeth, as described above. Graphically, the cut appears as the curve bounded by half the thickness of the cut on each side of the curve.

Figure 4:
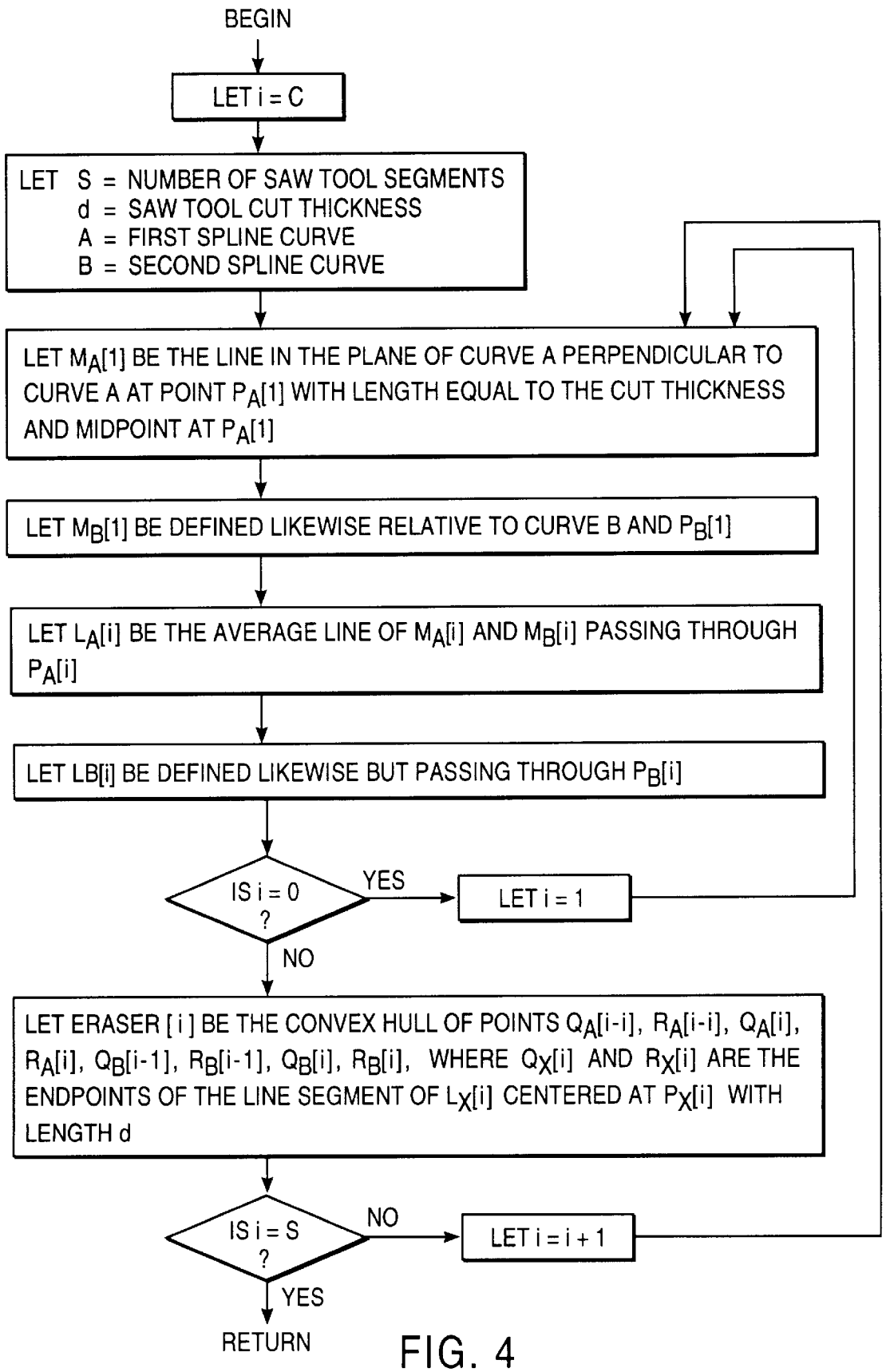
FIG. 4 is a flow chart illustrating an eraser tool for the methods herein.
Figure 4A:
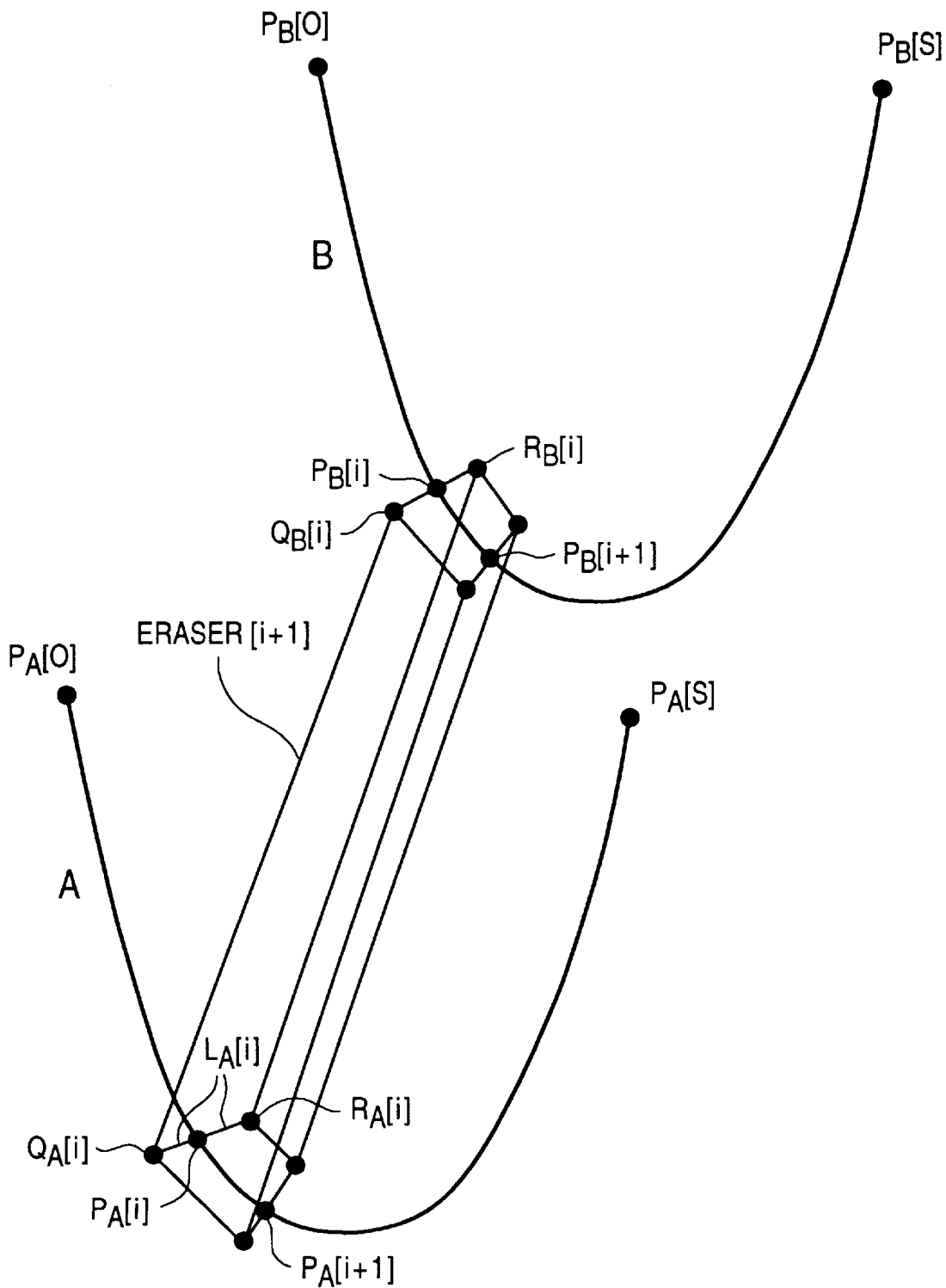
FIG. 4A illustrates the volume of space which is being erased by the program of FIG. 4.

Number of Erasers: A cut is comprised of multiple eraser boxes arranged next to each other as a piecewise linear approximation of the Saw Tool's curve path. The user chooses the number of erasers, which determines the sophistication of the curve created—the greater the number of segments, the more accurately the cutting will follow the curve. The number of erasers is shown graphically by the number of parallel lines connecting the two cubic B-spline curves. Once a saw cut has been completely specified the user applies the cut to the model. The cut is performed as a sequence of erasings. A preferred algorithm is set forth in FIG. 4. FIG. 4A shows a single erasing iteration of the cut as described in the algorithm.

A preview feature may also be provided in the software. The preview feature visually displays a saw cut as the two surfaces that represent opposed sides of the cut. This allows the user to consider the final cut before applying it to the model data set.

After the user has completed all desired cutting operations with the saw tool, multiple graphic solids exist. However, at this point, the software has not determined which triangles of the quad edge data structure belong to which components. The software chooses a random starting point in the data structure and traverses the data structure using adjacency information to find all of the triangles that are attached to each other, identifying an individual component. This process is repeated starting with the triangle whose component is not yet determined. Once the entire data structure is traversed, all components have been identified.

Figure 5:
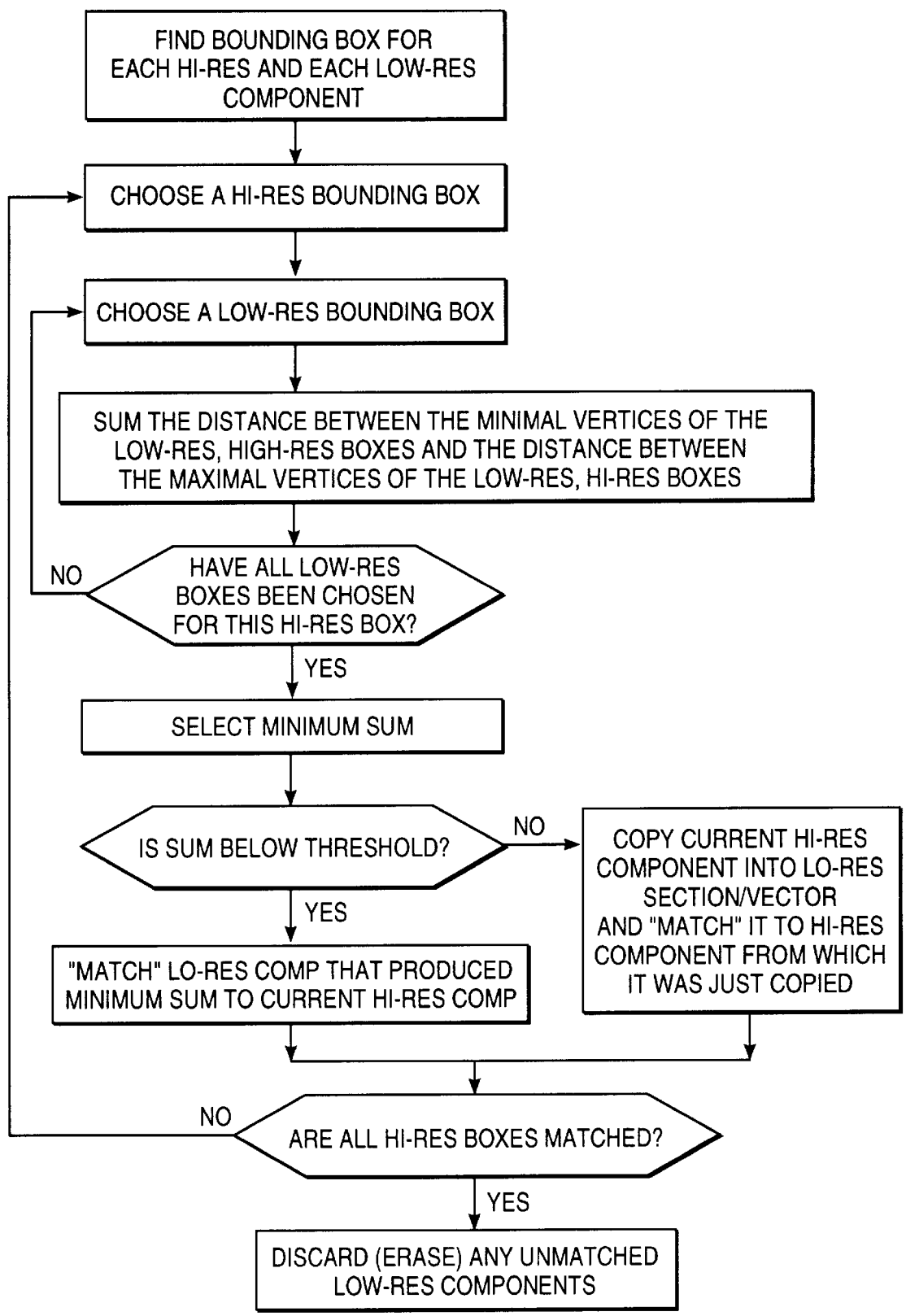
FIG. 5 is a flow chart illustrating a program for matching high-resolution and low-resolution components in the manipulation of data sets of FIG. 3.

To the user, all changes made to the high resolution model appear to occur simultaneously in the low resolution model, and vice versa. However, there is not a one-to-one correlation between the different resolution models. Therefore, the computer "matches" the high resolution and low resolution components as best as it can subject to defined limits. The algorithm is described in FIG. 5.

Figure 6:
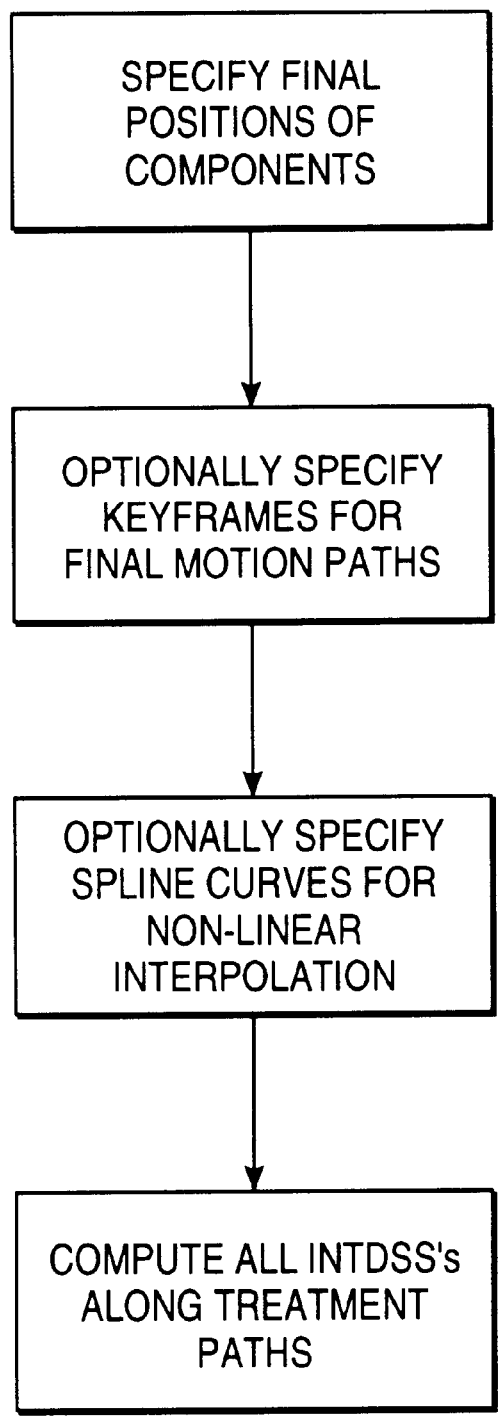
FIG. 6 illustrates the method for generating multiple intermediate digital data sets which are used for producing the adjustment appliances of the present invention.

After the teeth and other components have been placed or removed so that the final tooth arrangement has been produced, it is necessary to generate a treatment plan, as illustrated in FIG. 6. The treatment plan will ultimately produce the series of INTDDS's and FDDS as described previously. To produce these data sets, it is necessary to define or map the movement of selected individual teeth from the initial position to the final position over a series of successive steps. In addition, it may be necessary to add other features to the data sets in order to produce desired features in the treatment appliances. For example, it may be desirable to add wax patches to the image in order to define cavities or recesses for particular purposes. For example, it may be desirable to maintain a space between the appliance and particular regions of the teeth or jaw in order to reduce soreness of the gums, avoid periodontal problems, allow for a cap, and the like. Additionally, it will often be necessary to provide a receptacle or aperture intended to accommodate an anchor which is to be placed on a tooth in order to permit the tooth to be manipulated in a manner that requires the anchor, e.g. lifted relative to the jaw.

Some methods for manufacturing the tooth repositioning appliances require that the separate, repositioned teeth and other components be unified into a single continuous structure in order to permit manufacturing. In these instances, "wax patches" are used to attach otherwise disconnected components of the INTDDS's. These patches are added to the data set underneath the teeth and above the gum so that they do not effect the geometry of the tooth repositioning appliances. The application software provides for a variety of wax patches to be added to the model, including boxes and spheres with adjustable dimensions. The wax patches that are added are treated by the software as additional pieces of geometry, identical to all other geometries. Thus, the wax patches can be repositioned during the treatment path as well as the teeth and other components.

In the manufacturing process, which relies on generation of positive models to produce the repositioning appliance, adding a wax patch to the graphic model will generate a positive mold that has the same added wax patch geometry.

Because the mold is a positive of the teeth and the appliance is a negative of the teeth, when the appliance is formed over the mold, the appliance will also form around the wax patch that has been added to the mold. When placed in the patient's mouth, the appliance will thus allow for a space between the inner cavity surface of the appliance and the patient's teeth or gums. Additionally, the wax patch may be used to form a recess or aperture within the appliance which engages an anchor placed on the teeth in order to move the tooth in directions which could not otherwise be accomplished.

In addition to such wax patches, an individual component, usually a tooth, can be scaled to a smaller or larger size which will result in a manufactured appliance having a tighter or looser fit, respectively.

Treatment planning is extremely flexible in defining the movement of teeth and other components. The user may change the number of treatment stages, as well as individually control the path and speed of components.

Number of Treatment Stages: The user can change the number of desired treatment stages from the initial to the target states of the teeth. Any component that is not moved is assumed to remain stationary, and thus its final position is assumed to be the same as the initial position (likewise for all intermediate positions, unless one or more key frames are defined for that component).

Key frames: The user may also specify "key frames" by selecting an intermediate state and making changes to component position(s). Unless instructed otherwise, the software automatically linearly interpolates between all user-specified positions (including the initial position, all key frame positions, and the target position). For example, if only a final position is defined for a particular component, each subsequent stage after the initial stage will simply show the component an equal linear distance and rotation (specified by a quaternion) closer to the final position. If the user specifies two key frames for that component, it will "move" linearly from the initial position through different stages to the position defined by the first key frame. It will then move, possibly in a different direction, linearly to the position defined by the second key frame. Finally, it will move, possibly in yet a different direction, linearly to the target position.

The user can also specify non-linear interpolation between the key frames. A spline curve is used to specify the interpolating function in a conventional manner.

These operations may be done independently to each component, so that a key frame for one component will not affect another component, unless the other component is also moved by the user in that key frame. One component may accelerate along a curve between stages 3 and 8, while another moves linearly from stage 1 to 5, and then changes direction suddenly and slows down along a linear path to stage 10. This flexibility allows a great deal of freedom in planning a patient's treatment.

Lastly, the software may incorporate and the user may at any point use a "movie" feature to automatically animate the movement from initial to target states. This is helpful for visualizing overall component movement throughout the treatment process.

Above it was described that the preferred user interface for component identification is a three dimensional interactive GUI. A three-dimensional GUI is also preferred for component manipulation. Such an interface provides the treating professional or user with instant and visual interaction with the digital model components. It is preferred over interfaces that permit only simple low-level commands for directing the computer to manipulate a particular segment. In other words, a GUI adapted for manipulation is preferred over an interface that accepts directives, for example, only of the sort: "translate this component by 0.1 mm to the right." Such low-level commands are useful for fine-tuning, but, if they were the sole interface, the processes of component manipulation would become a tiresome and time-consuming interaction.

Before or during the manipulation process, one or more tooth components may be augmented with template models of tooth roots. Manipulation of a tooth model augmented with a root template is useful, for example, in situations where impacting of teeth below the gumline is a concern. These template models could, for example, comprise a digitized representation of the patient's teeth x-rays.

The software also allows for adding annotations to the datasets which can comprise text and/or the sequence number of the apparatus. The annotation is added as recessed text (i.e. it is 3-D geometry), so that it will appear on the printed positive model. If the annotation can be placed on a part of the mouth that will be covered by a repositioning appliance, but is unimportant for the tooth motion, the annotation may appear on the delivered repositioning appliance(s).

The above-described component identification and component manipulation software is designed to operate at a sophistication commensurate with the operator's training level. For example, the component manipulation software can assist a computer operator, lacking orthodontic training, by providing feedback regarding permissible and forbidden manipulations of the teeth. On the other hand, an orthodontist, having greater skill in intraoral physiology and teeth-moving dynamics, can simply use the component identification and manipulation software as a tool and disable or otherwise ignore the advice.

Figure 7:
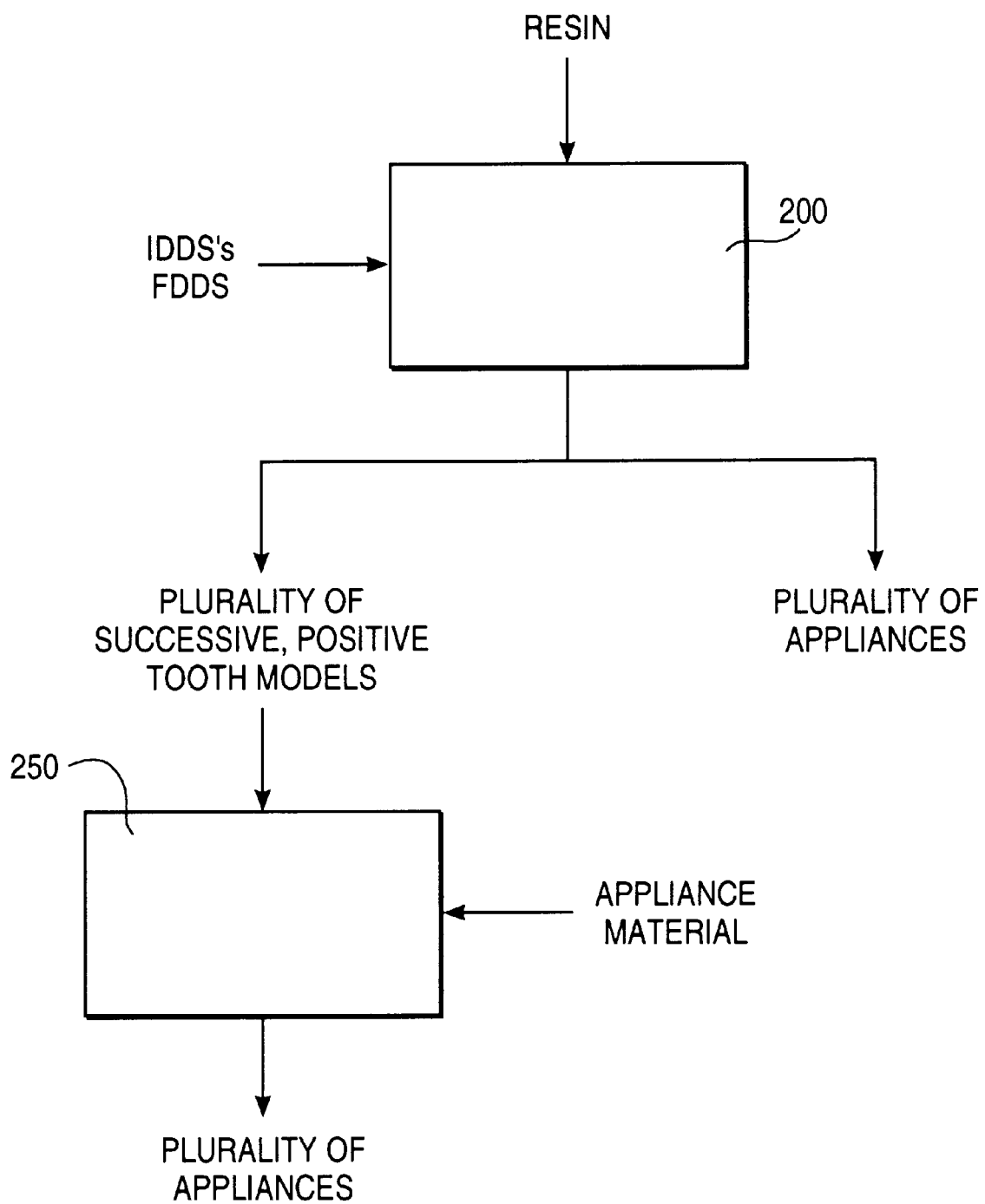
FIG. 7 illustrates alternative processes for producing a plurality of appliances according to the methods of the present invention utilizing digital data sets representing the intermediate and final appliance designs.

Once the intermediate and final data sets have been created, the appliances may be fabricated as illustrated in FIG. 7. Preferably, Fabrication methods will employ a rapid prototyping device 200 such as a stereolithography machine. A particularly suitable rapid prototyping machine is Model SLA-250/50 available from 3D System, Valencia, Calif. The rapid prototyping machine 200 will selectively harden a liquid or other non-hardened resin into a three-dimensional structure which can be separated from the remaining non-hardened resin, washed, and used either directly as the appliance or indirectly as a mold for producing the appliance. The prototyping machine 200 will receive the individual digital data sets and produce one structure corresponding to each of the desired appliances. Generally, because the rapid prototyping machine 200 may utilize a resin having non-optimum mechanical properties and which may not be generally acceptable for patient use, it will be preferred to use the prototyping machine to produce molds which are, in effect, positive tooth models of each successive stage of the treatment. After the positive models are prepared, a conventional pressure or vacuum molding machine may be used to produce the appliances from a more suitable material, such as 0.03 inch thermal forming dental material, available from Tru-Tain Plastics, Rochester, Minn. 55902. Suitable pressure molding equipment is available under the tradename BIOSTAR from Great Lakes Orthodontics, Ltd., Tonawanda, N.Y. 14150. The molding machine 250 produces each of the appliances directly from the positive tooth model and the desired material. Suitable vacuum molding machines are available from Raintree Essix, Inc.

After production, the plurality of appliances which comprise the system of the present invention are preferably supplied to the treating professional all at one time. The appliances will be marked in some manner, typically by sequential numbering directly on the appliances or on tags, pouches, or other items which are affixed to or which enclose each appliance, to indicate their order of use. Optionally, written instructions may accompany the system which set forth that the patient is to wear the individual appliances in the order marked on the appliances or elsewhere in the packaging. Use of the appliances in such a manner will reposition the patient's teeth progressively toward the final tooth arrangement.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A system for repositioning teeth from an initial tooth arrangement to a final tooth arrangement, said system comprising a plurality of dental incremental position adjustment appliances including:
    a first appliance having a geometry selected to reposition the teeth from the initial tooth arrangement to a first intermediate arrangement;
    one or more intermediate appliances having geometries selected to progressively reposition the teeth from the first intermediate arrangement to successive intermediate arrangements; and
    a final appliance having a geometry selected to progressively reposition the teeth from the last intermediate arrangement to the final tooth arrangement, wherein the appliances comprise polymeric shells having cavities and wherein the cavities of successive shells have different geometries shaped to receive and resiliently reposition teeth from one arrangement to a successive arrangement.

2. A system as in claim 1, wherein the tooth positions defined by the cavities in each successive appliance differ from those defined by the prior appliance by no more than 2 mm.

3. A system as in claim 1, comprising at least two intermediate appliances.

4. A system as in claim 3, comprising at least ten intermediate appliances.

5. A system as in claim 4, comprising at least twenty-five intermediate appliances.

6. A method for repositioning teeth from an initial tooth arrangement to a final tooth arrangement, said method comprising:
    placing a first incremental position adjustment appliance in a patient's mouth, wherein the first appliance has a geometry selected to reposition the teeth from the initial tooth arrangement to a first intermediate arrangement;
    successively replacing one or more additional appliances, wherein the additional appliances have geometries selected to progressively reposition the teeth from the first intermediate arrangement to successive intermediate arrangements; and
    placing a final appliance into the patient's mouth, wherein the final appliance has a geometry selected to progressively reposition the teeth from the last intermediate arrangement to the final tooth arrangement, wherein the appliances comprise polymeric shells having cavities shaped and wherein the cavities of successive shells have difficult geometries to receive and resiliently reposition teeth from one arrangement to a successive arrangement.

7. A method as in claim 6, where the tooth positions defined by the cavities in each successive appliance differ from those defined by the prior appliance by no more than 2 mm.

8. A method as in claim 6, wherein the successively placing step comprises placing at least two additional appliances prior to placing the final appliance.

9. A method as in claim 8, wherein the successively placing step comprises placing at least ten additional appliances.

10. A method as in claim 9, wherein the successively placing step comprises placing at least twenty-five additional appliances.

11. A method as in claim 6, wherein the appliances are successively replaced at an interval in the range from 2 days to 20 days.

12. An improved method for repositioning teeth using appliances comprising polymeric shells having cavities shaped to receive and resiliently reposition teeth to produce a final tooth arrangement, wherein the improvement comprises determining at the outset of treatment geometries for at least three appliances which are to be worn successively by a patient to reposition teeth from an initial tooth arrangement to the final tooth arrangement, wherein the cavities of successive shells have different geometries.

13. An improved method as in claim 12, wherein at least four geometries determined at the outset.

14. An improved method as in claim 13, wherein at least ten geometries are determined at the outset.

15. An improved method as in claim 14, wherein at least twenty-five geometries are determined at the outset.

16. An improved method as in claim 12, wherein the tooth positions defined by the cavities in each successive appliance differ from those defined by the prior appliance by no more than 2 mm.

17. A system for repositioning teeth from an initial tooth arrangement to a final tooth arrangement, said system comprising a plurality of dental incremental position adjustment appliances including:
    a first appliance having a geometry selected to reposition the teeth from the initial tooth arrangement to a first intermediate arrangement;
    one or more intermediate appliances having geometries selected to progressively reposition the teeth from the first intermediate arrangement to successive intermediate arrangements; and
    a final appliance having a geometry selected to progressively reposition the teeth from the last intermediate arrangement to the final tooth arrangement, wherein the appliances comprise polymeric shells having cavities shaped to receive and resiliently reposition teeth from one arrangement to a successive arrangement and wherein the tooth positions defined by the cavities in each successive appliance differ from those defined by the prior appliance by no more than 2 mm.

18. A system as in claim 17, comprising at least two intermediate appliances.

19. A system as in claim 18, comprising at least ten intermediate appliances.

20. A system as in claim 19, comprising at least twenty-five intermediate appliances.

21. A method for repositioning teeth from an initial tooth arrangement to a final tooth arrangement, said method comprising:
    placing a first incremental position adjustment appliance in a patient's mouth, wherein the first appliance has a geometry selected to reposition the teeth from the initial tooth arrangement to a first intermediate arrangement;

successively replacing one or more additional appliances, wherein the additional appliances have geometries selected to progressively reposition the teeth from the first intermediate arrangement to successive intermediate arrangements; and placing a final appliance into the patient's mouth, wherein the final appliance has a geometry selected to progressively reposition the teeth from the last intermediate arrangement to the final tooth arrangement, wherein the appliances comprise polymeric shells having cavities shaped to receive and resiliently reposition teeth from one arrangement to a successive arrangement, and wherein the tooth positions defined by the cavities in each successive appliance differ from those defined by the prior appliance by no more than 2 mm.

22. A method as in claim 21, wherein the successively placing step comprises placing at least two additional appliances prior to placing the final appliance.

23. A method as in claim 22, wherein the successively placing step comprises placing at least ten additional appliances.

24. A method as in claim 23, wherein the successively placing step comprises placing at least twenty-five additional appliances.

25. A method as in claim 21, wherein the appliances are successively replaced at an interval in the range from 2 days to 20 days.

26. An improved method for repositioning teeth using appliances comprising polymeric shells having cavities shaped to receive and resiliently reposition teeth to produce a final tooth arrangement, wherein the improvement comprises determining at the outset of treatment geometries for at least three appliances which are to be worn successively by a patient to reposition teeth from an initial tooth arrangement to the final tooth arrangement, wherein the tooth positions defined by the cavities in each successive appliance differ from those defined by the previous appliance by no more than 2 mm.

27. An improved method as in claim 26, wherein at least four geometries determined at the outset.

28. An improved method as in claim 27, wherein at least ten geometries are determined at the outset.

29. An improved method as in claim 28, wherein at least twenty-five geometries are determined at the outset.

* * * * *

(12) EX PARTE REEXAMINATION CERTIFICATE (6397th)
United States Patent
Chishti et al.

(10) Number: US 5,975,893 C1
(45) Certificate Issued: Aug. 26, 2008

(54) METHOD AND SYSTEM FOR INCREMENTALLY MOVING TEETH

(75) Inventors: Muhammad Chishti, Menlo Park, CA (US); Apostolos Lerios, Stanford, CA (US); Brian Freyburger, Palo Alto, CA (US); Kelsey Wirth, Menlo Park, CA (US); Richard Ridgley, Los Altos, CA (US)

(73) Assignee: Align Technology, Inc., Redwood City, CA (US)

Reexamination Request:
No. 90/007,477, Mar. 22, 2005

Reexamination Certificate for:
Patent No.: 5,975,893
Issued: Nov. 2, 1999
Appl. No.: 08/947,080
Filed: Oct. 8, 1997

Related U.S. Application Data

(60) Provisional application No. 60/050,342, filed on Jun. 20, 1997.

(51) Int. Cl.
*A61C 3/00* (2006.01)

(52) U.S. Cl. .............................. 433/6; 433/24
(58) Field of Classification Search ...................... 433/6, 433/18, 20, 24
See application file for complete search history.

(56) References Cited

U.S. PATENT DOCUMENTS

| | | |
|---|---|---|
| 2,467,432 A | 4/1949 | Kesling |
| 3,407,500 A | 10/1968 | Kesling |
| 3,600,808 A | 8/1971 | Reeve |
| 3,683,502 A | 8/1972 | Wallshein |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |

(Continued)

FOREIGN PATENT DOCUMENTS

| | | |
|---|---|---|
| AU | 3031677 | 5/1979 |
| AU | 5598894 | 6/1994 |
| CA | 1121955 | 4/1982 |

(Continued)

OTHER PUBLICATIONS

Alexander et al., "The DigiGraph Work Station Part 2, Clinical Management," *JCO* (Jul. 1990), pp. 402–407.

(Continued)

*Primary Examiner*—Michael O'Neill

(57) ABSTRACT

A system for repositioning teeth comprises a plurality of individual appliances. The appliances are configured to be placed successively on the patient's teeth and to incrementally reposition the teeth from an initial tooth arrangement through a plurality of intermediate tooth arrangements, and to a final tooth arrangement. The system of appliances is usually configured at the outset of treatment so that the patient may progress through treatment without the need to have the treating professional perform each successive step in the procedure.

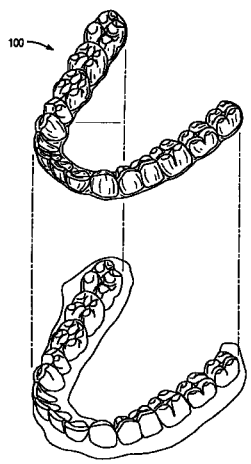

U.S. PATENT DOCUMENTS

| Patent Number | Date | Inventor |
|---|---|---|
| 4,742,464 A | 5/1988 | Duret et al. |
| 4,763,791 A | 8/1988 | Halverson et al. |
| 4,793,803 A | 12/1988 | Martz |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,937,928 A | 7/1990 | Van Der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,027,281 A | 6/1991 | Rekow et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,257,203 A | 10/1993 | Riley et al. |
| 5,278,756 A | 1/1994 | Lemchen et al. |
| 5,368,478 A | 11/1994 | Andreiko et al. |
| 5,440,326 A | 8/1995 | Quinn |
| 5,440,496 A | 8/1995 | Andersson et al. |
| RE35,169 E | 3/1996 | Lemchen et al. |
| 5,518,397 A | 5/1996 | Andreiko et al. |
| 5,528,735 A | 6/1996 | Strasnick et al. |
| 5,562,448 A | 10/1996 | Mhabac |
| 5,614,075 A | 3/1997 | Andre |
| 5,621,648 A | 4/1997 | Crump |
| 5,645,420 A | 7/1997 | Bergersen |
| 5,655,653 A | 8/1997 | Chester |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | Van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |
| 6,398,548 B1 | 6/2002 | Muhammad et al. |
| 6,524,101 B1 | 2/2003 | Phan et al. |
| 6,554,611 B2 | 4/2003 | Chishti et al. |
| 6,629,840 B2 | 10/2003 | Chishti et al. |
| 6,705,863 B2 | 3/2004 | Phan |
| 2002/0006597 A1 | 1/2002 | Andreiko et al. |

FOREIGN PATENT DOCUMENTS

| | | |
|---|---|---|
| DE | 2749802 | 5/1978 |
| DE | 69327661 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0667753 | 8/1995 |
| EP | 0774933 B1 | 5/1997 |
| EP | 0541500 A1 | 6/1998 |
| EP | 0731673 B1 | 9/1998 |
| ES | 0463897 | 1/1980 |
| FR | 2652256 A1 | 3/1991 |
| GB | 1550777 | 8/1979 |
| JP | 53-058191 | 5/1978 |
| JP | 0428359 | 1/1992 |
| JP | 04028359 * | 1/1992 |
| JP | 08-508174 | 9/1996 |
| WO | WO 90/08512 A1 | 8/1990 |
| WO | WO 91/04713 A1 | 4/1991 |
| WO | WO 98/32394 | 7/1998 |
| WO | WO 98/44865 A1 | 10/1998 |
| WO | WO 98/58596 A1 | 12/1998 |

OTHER PUBLICATIONS

Altschuler et al, "Measuring Surfaces Space–Coded by a Laser–Projected Dot Matrix," *SPIE Imaging Applications for Automated Industrial Inspection and Assembly*, vol. 182 (1979), p. 187–191.

Altschuler et al., "Analysis of 3–D Data for Comparative 3–D Serial Growth Pattern Studies of Oral–Facial Structures," IADR Abstracts, Program and Abstracts of Papers, 57th General Session, IADR Annual Session, Mar. 29, 1979–Apr. 1, 1979, New Orleans Marriot, *Journal of Dental Research*, vol. 58, Jan. 1979, Special Issue A, p. 221.

Altschuler et al., "Laser Electro–Optic System for Rapid Three–Dimensional (3D) Topographic Mapping of Surfaces," *Optical Engineering*, vol. 20(6) (1981), pp. 953–961.

Altschuler, "3D Mapping of Maxillo–Facial Prosthesis," AADR Abstract #607, 1980.1 page total.

American Association for Dental Research, Summary of Activities, Mar. 20–23, 1980, Los Angeles, CA, p. 195.

Andersson et al., "Clinical Results with Titanium Crowns Fabricated with Machine Duplication and Spark Erosion," *Acta Odontological Scandinavia*, vol. 47 (1989), pp. 279–286.

Baumrind et al., "A Stereophotogrammetric System for the Detection of Prosthesis Loosening in Total Hip Arthroplasty," NATO Symposium on Applications of Human Biostereometrics, Jul. 9–13, 1978, SPIE vol. 166, pp. 112–123.

Baumrind et al., "Mapping the Skull in 3–D," Reprinted from The Journal, *California Dental Association*, vol. 48, No. 2 (1972 Fall Issue) 11 pages total.

Baumrind, "A System for Craniofacial Mapping Through the Integration of Data from Stereo X–Ray Films and Stereo Photographs," An invited paper submitted to the 1975 American Society of Photogram. Symposium on Close–Range Photogram. Systems, University of Il., Aug. 26–30, 1975, pp. 142–166.

Baumrind, "Integrated Three–Dimensional Craniofacial Mapping: Background, Principles, and Perspectives," *Seminars in Orthodontics*, vol. 7, No. 4 (Dec. 2001), pp. 223–232.

Begole et al., "A Computer System for the Analysis of Dental Casts," *The Angle Orthodontist*, vol. 51, No. 3 (Jul. 1981), pp. 253–259.

Bernard et al., "Computerized Diagnosis in Orthodontics for Epidemiological Studies: A Progress Report," Abstracts of Papers, *Journal of Dental Research*; vol. 67, Special Issue Mar. 9–13, 1988, J3.p.169.

Bhatia et al,, "A Computer–Aided Design for Orthognathic Surgery," *British Journal of Oral and Maxillofacial Surgery*, vol. 22 (1984), pp. 237–253.

Biggerstaff et al., "Computerized analysis of occlusion in the postcanine dentition, American Journal of Orthodontics," vol. 61, No. 3 (Mar. 1972), pp. 245–254.

Biggerstaff, "Computerized Diagnostic Setups and Simulations," *The Angle Orthodontist*, vol. 40, No. 1 (Jan. 1970), pp. 28–36.

Boyd et al., "Three Dimensional Diagnosis and Orthodontic Treatment of Complex Malocclusions WIith the Invisalign Appliance," *Seminars in Orthodontics*, vol. 7, No. 4 (Dec. 2001), p. 274–293.

Brandestini et al., "Computer Machined Ceramic Inlays: In Vitro Marginal Adaptation," *Journal of Dental Research*, vol. 64/Special Issue/Abstracts, IADR/AADR Abstracts 1985, p. 208.

Brook et al., "An Image Analysis System for the Determination of Tooth Dimensions from Study Casts: Comparison with Manual Measurements of Mesio–distal Diameter," *J Dent Res.*, vol. 65, No. 3, Mar. 1986, pp. 428–431.

Burstone (interview), "Dr. Charles J. Burstone on The Uses of the Computer in Orthodontic Practice (Parts 1and 2)," *Journal of Clinical Orthodontics*, (Part 1) vol. 8, No. 7 , Jul. 1979; (Part 2) vol. 8, No. 8 pp. 539–551, Aug. 1979.

Burstone et al., "Precision adjustment of the transpalatal lingual arch: Computer arch form predetermination," *Am. Journal of Orthodontics*, vol. 79, No. 2 (Feb. 1981), pp. 115–133.

Chaconas et al., "The DigiGraph Wori<Station, Part 1, Basic Concepts," *JCO* (Jun. 1990), pp. 360–367.

Chafetz et al., "Subsidence of the Femoral Prosthesis, A Stereophotogrammetric Evaluation," *Clinical Orthopaedics and Related Research*, No. 201 (Dec. 1985), pp. 60–67.

Crawford, "CAD/CAM in the Dental Office: Does It Work!" *Canadian Dental Journal*, vol. 57, No. 2 (Feb. 1991), pp. 121–123.

Crawford, "Computers in Dentistry: Part 1: CAD/CAM: The Computer Moves Chairside," "Part 2: F. Duret—A Man With A Vision," "Part 3: The Computer Gives New Vision— Literally," "Part 4: Bytes 'N Bites" The Computer Moves From The Front Desk To The Operator/, *Canadian Dental Journal*, vol. 54(9), (1988), pp. 661–666.

Crooks, "CAD/CAM Comes to USC," *USC Dentistry*, (Spring 1990) pp. 14–17.

Cutting et.al., "Three–Dimensional Computer–Assisted Design of Craniofacial Surgical Procedures: Optimization and Interaction with Cephalometric and CT–Based Models," *Plastic and Reconstructive Surgery*, vol. 77. No. 6 (Jun. 1986). pp. 877–885.

DCS Dental AG, "The CAD/CAM 'DCS Titan System' for Production of Crowns/Bridges" *DSC Production AG*, Jan. 1992, pp. 1–7.

Dental Institute University of Zurich Switzerland, Program for International Symposium on Computer Restorations: State of the Art of the CEREC–Method, May 1991, 2 pages total.

Duret et al, "CAD–CAM in Dentistry," *Journal of the American Dental Association*, vol. 117 (Nov. 1988), pp. 715–720.

Duret et al., "CAD/CAM Imaging in Dentistry," *Current Opinion in Dentistry*, vol. 1 (1991), pp. 150–154.

Duret, "The Dental CAD/CAM, General Description of the Project," *Hennson International Product Brochure*, Jan. 1986., 18 pages total.

Duret, "Vers une prosthese informatisee," (English translation also attached), *Tonus*, vol. 75, (Nov. 15, 1985), pp. 55–57.

Economides, "The Microcomputer in the Orthodontic Office," *JCO*, (Nov. 1979), pp. 767–772.

Faber et al., "Computerized interactive orthodontic treatment planning," *Am. J. Orthod.*, vol. 73, No. 1 (Jan. 1978), pp. 36–46.

Felton et al. "A computerized analysis of the shape and stability of mandibular arch form," *Am. Journal of Orthodontics and Dentofacial Orthopedics*, vol. 92, No. 6 (Dec. 1987), pp. 478–483.

Friede et al., "Accuracy of Cephalometric Prediction in Orthognathic Surgery," Abstract of Papers, *Journal of Dental Research*, vol. 70 (1987), pp. 754–760.

Gim–Alldent Deutschland, "Das DUX System: Die Technik," 2 pages total.

Grayson, "New Methods for Three Dimensional Analysis of Craniofacial Deformity," Symposium: Computerized Facial Imaging in Oral and Maxilofacial Surgery, Presented on Sep. 13, 1990, AAOMS 72nd Annual Meeting and Scientific Sessions, Sep. 13, 1990, New Orleans, *Journal of Oral and Maxillofacial Surgery*, vol. 48, No. 8, Supp. 1, Aug. 1990, pp. 5–6.

Guess et al., "Computer Treatment Estimates In Orthodontics and Orthognathic Surgery," *JCO*, (Apr. 1989), pp. 262–28.

Heaven et al., "Computer–based Image Analysis of Artificial Root Surface Caries," Abstracts of Papers, *Journal of Dental Research*, vol. 70,Apr. 17–21, 1991, p. 528.

Hoffmann et al,, "Role of Cephalometry for Planning of Jaw Orthopedics and Jaw Surgery Procedures," (Article Summary In English, article in German), *Informationen*, (Mar. 1991), pp. 375–396.

Huckins, "CAD–CAM Generated Mandibular Model Prototype from MRI Data," *AAOMS* 1999, p. 96.

JCO Interviews, "Craig Andreiko , DDS, MS on the Elan and Orthos Systems," *JCO*, (Aug. 1994), pp. 459–468.

JCO Interviews, "Dr. Homer W. Phillips on Computers in Orthodontic Practice, Part 2," *JCO*, (Dec. 1983), pp. 819–831.

Jerrold, "The Problem, Electronic Data Transmission and the Law," *AJO–DO*, (Apr. 1988), pp. 478–479.

Jones et al., "An Assessment of the Fit of a Parabolic Curve to Pre– and Post–Treatment Dental Arches," *British Journal of Orthodontics*, vol. 16 (1989), pp. 85–93.

Kanazawa et al., "Three–Dimensional Measurements of the Occlusal Surfaces of Upper Molars in a Dutch Population," *J. Dent Res.*, vol. 63, No. 11 (Nov. 1984), pp. 1298–1301.

Laurendeau et al, "A Computer–Vision Technique for the Acquisition and Processing of 3–D Profiles of Dental Imprints: An Application in Orthodontics," *IEEE Transactions on Medical Imaging*, vol. 10, No. 3 (Sep. 1991), pp. 453–461.

Leinfelder et al, "A new method for generating ceramic restorations: a CAD–CAM system," *Journal Of The American Dental Assoc.*, vol. 118, No. 6 (Jun. 1989), pp. 703–707.

Manetti et al., "Computer–aided Cefalometry and New Mechanics in Orthodontics" (Article Summary in English, article in German), *Fortschr. Kieferorthop.* 44, 370–376 (Nr. 5), 1983.

McCann, Inside the ADA, *Journal Of The American Dental Assoc.*, vol. 118 (Mar. 1989) pp. 286–294.

McNamara et al, "Invisible Retainers," *J. Clinical Orthodontics*, (Aug. 1985) pp. 570–578.

McNamara et al., Chapter 19: Invisible Retainers. *Orthodontic and Orthopedic Treatment in the Mixed Dentition*, Needham Press, Jan. 1993. pp. 347–353.

Moermann et al, "Computer Machined Adhesive Porcelain Inlays: Margin Adaptation after Fatigue Stress," IADR Abstract 339, *Journal of Dental Research*, vol. 66(a) (1987), p. 763.

Moermann et al., "Marginal Adaptation von adhasiven Porzellaninlays in vitro," *Schwizerische Monatsshrift fur Zahnmedizin*, vol. 85 (1985), p. 1118–1129.

Nash, "Cerec CAD/CAM Inlays: Aesthetics and Durability in a Single Appointment," *Dentistry Today*, (Oct. 1990), pp. 20, 22–23, 54.

Pinkham, "'Foolish' Concept Propels Technology," *Dentist*, Jan./Feb. 1989,3 pages total.

Pinkham, "Inventor's CAD/CAM May Transform Dentistry," *Dentist*, Sep. 1990, 3 pages total.

Procera Research Projects, *Procera Research Projects* 1993—Abstract Collection, 1993, pp. 3–24.

Rekow, "A Review of the Developments in Dental CAD/CAM Systems,"(contains references to Japanese efforts and content of the papers of particular interest to the clinician are indicated with a one–line summary of their content in the bibliography), Dental Clinics: *Prosthodontics and Endodontics*, pp. 25–33, 1992.

Rekow, "CAD/CAM in Dentistry: A Historical Perspective and View of the Future," *Journal*, vol. 58 No. 4, (Apr. 1992), pp. 283, 287–288.

Rekow, "Computer–Aided Design and Manufacturing in Dentistry: A Review of the State of the Art," *The Journal of Prosthetic Dentistry*, vol. 58, No. 4 (Oct. 1987), pp. 512–516.

Rekow, "Dental CAD–CAM Systems: What is the State of the Art!" *Journal of the American Dental Assoc.*, vol. 122 (1991), pp. 43–48.

Richmond et al., Research Reports, "The, Development of a 3D Cast Analysis System," *British Journal of Orthodontics*, vol. 13, No. 1, (Jan. 1986), pp. 53–54.

Richmond, "Recording The Dental Cast In Three Dimensions," *Am. J. Orthod. Dentofac. Orthop.*, vol. 92, No. 3, (Sep. 1987), pp. 199–206.

Rudge, "Dental arch analysis: arch form, A review of the literature," *European Journal of Orthodontics*, vol. 3, No. 4 (1981), pp. 279–284.

Sakuda et al., "Integrated information–processing system In clinical orthodontics: An approach with use of a computer network system," *Am. J. Orthod. Dentofac. Orthop.* vol. 101 No. 3 (Mar. 1992), pd. 210–220.

Schellhas et al., "Three–Dimensional Computed Tomography in Maxillofacial Surgical Planning," *Arch Otolamgol Head Neck Surg.* vol. 114 (Apr. 1988), pp. 438–442.

Siemens, CEREC—Computer–Reconstruction, "High Tech in der Zahnmedizin," 14 page total.

Sirona Dental Systems GmbH, CEREC 3D, Manuel utiiisateur, Version 2.0X (in French), 2003, 114 pages total.

Stoll et al., "Computer–aided Technologies in Dentistry" (Article Summary in English, article in German), *Dtsch Zahnärztl Z* 45, 314–322,1990.

U.S. Department of Commerce, National Technical Information Service, "Automated Crown Replication Using Solid Photography SM," Solid Photography Inc. Melville NY, Oct. 1977, 20 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/0503,42, filed Jun. 20, 1997, 41 pages total.

Van Der Linden et al., "Three–Dimensional Analysis of Dental Casts by Means of the Optocom," *J Dent Res*, Jul.–Aug. 1972, p. 1101.

Van Der Linden, "A New Method to Determine Tooth Positions and Dental Arch Dimensions," Jul.–Aug. 1972, p. 1104.

Varady et al., "Reverse Engineering of Geometric Models—An Introduction, Computer–Aided Design," 29 (4):255–268, 1997.

Williams, "Dentistry and CAD/CAM: Another French Revolution," *Journal of Dental Practice Admin.*, Jan./Mar. 1987, pp. 2–5.

Williams, "The Switzerland and Minnesota Developments in CAD/CAM," *Journal of Dental Practice Admin.*, pp. 50–55, Apr./Jun. 1987.

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990, AAOMS 72nd Annual Meeting and Scientific Sessions, Sep. 13, 1990, New Orleans, *Journal of ORal and Mixillofacial Surgery*, vol. 48, No. 8, Supp. 1, Aug. 1990, p. 5.

Yamamoto et al., "Optical measurement of dental cast profile and application to analysis of three–dimensional tooth movement in orthodontics," *Frontiers in Med. and Biol. Eng'g*, vol. 1, No. 2 (1988), pp. 119–130.

Yamamoto et al., "Three–Dimensional Measurement of Dental Cast Profiles and Its Applications to Orthodontics," Annual Int'l Conf. of IEEE Engineering in Medicine and Biology Society, vol. 12, No. 5, pp. 2051–2053, 1990.

Alcaniz, et al., "An Advanced System for the Stimulation and Planning of Orthodontic Treatments", *Visualization in Biomedical Computing*, eds. Hohne and Kikinis, Springer–Verlag, (Sep. 1996) pp. 511–520.

Andrews, "Straight Wire, The Concept and Appliance," *The Six Keys to Optimal Occlusion*, Chapter 3, pp. 13–24.

Bartels, et al, An Introduction to Splines for Use in Computer Graphics and Geometric Modeling, Morgan Kaufmann Publishers, (1987) 422–425.

Blu, et al., "Linear interpolation revitalized", *IEEE Transaction on Image Processing*, (May 2004) 13(5): 710–719.

Cardinal Industrial Finishes, Powder Coatings information posted at http://www.cardinalpaint.com on Aug. 25, 2000, 6 pages total.

Curry et al., "Integrated Three–Dimensional Craniofacial Mapping at the Craniofacial Research Instrumentation Laboratory/University of the Pacific," *Seminars in Orthodontics*, vol. 7, No. 4 (Dec. 2001), pp. 258–265.

DeFranco et al., "Three–Dimensional Large Displacement Analysis of Orthodontic Appliances," *J. Biomechanics*, vol. 9 (1976), pp. 793–801.

Dentrac Corporation, Dentrac document, pp. 4–13.

Dent–X posted at http://www.dent–x.com/DentSim.htm Sep. 24, 1998, 6 pages total.

Doyle, (2000). "Digital Dentistry," *Computer Graphics World*, Oct. 2000 pp. 50–52, 54.

Fütterling et al., "Automated Finite Element Modeling of a Human Mandible with Dental Implants," WSCG '98—Conference Program, retrieved from the Internet: <<http://wscg.zcu.cz/wscg98/papers98/Strasser_98.pdf.>>, 8 pages total.

Hikage, "Integrated Orthodontic Management System for Virtual Three–Dimensional Computer Graphic Simulation and Optical Video Image Database for Diagnosis and Treatment Planning", *Journal of Japan Orthodontic Society*, (Feb. 1987), English translation, pp. 1–38, Japanese version, 46(2): 248–269 (60 pages total).

Hojjatie et al., "Three–Dimensional Finite Element Analysis of Glass–Ceramic Dental Crowns," *J. Biomech.* (1990) vol. 23, No. 11, pp. 1157–1166.

Kochanek, "Interpolating Splines with Local Tension, Continuity and Bias Control", *Computer Graphics*, (Jul. 1984) 18(3): 33–41.

Kunii et.al., "Articulation Simulation for an Intelligent Dental Care System," *Displays*, vol. 15, No. 3 (1994), pp. 181–188.

Procera Research Projects, Procera Research Projects 1993—Abstract Collection, 1993, pp. 3–24.

Proffit et al, Contemporary Orthodontics (Second Ed.) Chapter 15, Mosby Inc., (Oct. 1992), pp. 470–533.

Redmond et al. "Clinical Implications of Digital Orthodontics," *Am. J. Orthodont. Dentofacial Orthopedics*, vol. 117, No. 2 (2001), pp. 240–242.

Rekow et al., "CAD/CAM for Dental Restorations—Some of the Curious Challenges," *IEEE Transactions on Biomedical Engineering*, (Apr. 1991) vol. 38, No. 4, pp. 314–318.

Rekow et al., "Comparison of Three Data Acquisition Techniques for 3–D Tooth Surface Mapping," *Annual International Conference of the IEEE Engineering in Medicine and Biology Society*, (1991) vol. 13, No. 1, pp. 344–345.

Rekow, "Feasibility of an Automated System for Production of Dental Restorations," PhD Thesis, Univ. of Minnesota, Nov. 1988, 244 pages total.

Richmond et. al., "the Development of the PAR Index (Peer Assessment Rating): Reliability and Validity," *European Journal of Orthodontics* (1992) 14:125–139.

Schroeder et al., Eds. Chapters 6, 8, 9, The Visual Toolkit, Prentice Hall PTR, New Jersey (1998), (pp. 153–209, 309–353, and 355–427, respectively).

Sturman, "Interactive Keyframe Animation of 3–D Articulated Models," *Proceedings Graphics Interface '84*, (May–Jun. 1984) pp. 35–40.

Tru–Tain Orthodontic & Dental Supplies, Product Brochure, Rochester, Minnesota 55902, 16 pages total.

Van Der Zel, "Ceramic–fused–to–metal Restorations with a New CAD/CAM System," *Quintessence International*, vol. 24(11) (Nov. 1993), pp. 769–778.

Nahoum, H. I. (Nov. 1964). "The vacuum formed dental contour appliance," *The New York State Dental Journal* 30(9): 385–390.

Ponitz, R. J. (Mar. 1971). "Invisible retainers," *Am. J. Orthod.* 59 (3):266–72.

Gottleib and McNamara. (Jun. 1982). "JCO Interviews Dr. James A. McNamara, Jr., on the Frankel Appliance, Part 2: Clinical Management," *Journal of Clinical Orthodontics* 16(6): 390–407.

Sinclair, Peter M. (Jun. 1992). "The Readers' Corner," *Journal of Clinical Orthodontics* 26(6): 369–372.

Warunek et al. (May 1989). "Physical and mechanical properties of elastomers in orthodontic positioners," *Am. J. Orthod. Dentofac. Orthop.* 95(5): 388–400.

Declaration of Richard Ridgley, Mar. 16, 2005, total pages 5.

Deposition Transcript of Lloyd Truax, D.D.S., Case No. SACV:03–16 GLT(ANX), *Ormco Corporation v. Align Technology, Inc.*, (Dec. 3, 2004), total pages. 51.

Deposition Transcript of Kevin L. Truax, Case No. SACV:03–16 GLT(ANX), *Ormco Corporation v. Align Technology, Inc.*, (Dec. 3, 2004), total pages. 57.

Documents produced by Lloyd and Kevin Truax, Case No. SACV:03–16 GLT(ANX), *Ormco Corporation v. Align Technology, Inc.*, total pages 63.

Deposition Transcript of Michael David Rains, D.D.S., Case No. SACV:03–16 GLT(ANX), *Ormco Corporation v. Align Technology, Inc.* (Nov. 15, 2004) total pp. 57.

Deposition Transcript of Michael David Rains, D.D.S., Case No. SACV:03–16 GLT(ANX), *Ormco Corporation v. Align Technology, Inc.*, (Nov. 15, 2004) total pp. 14.

Documents produced by Guadalupe Nieto, Case No. SACV:03–16 GLT(ANX), *Ormco Corporation v. Align Technology, Inc.*, total pages 33.

* cited by examiner dd
EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 6, 12–15, 17, 21 and 26–29 are determined to be patentable as amended.

Claims 2–5, 7–11, 16, 18–20 and 22–25, dependent on an amended claim, are determined to be patentable.

New claims 30–58 are added and determined to be patentable.

1. A system for repositioning teeth from an initial tooth arrangement to a final tooth arrangement, said system comprising a plurality of dental incremental position adjustment appliances including:
   a first appliance having a geometry selected to reposition the teeth from the initial tooth arrangement to a first intermediate arrangement;
   one or more intermediate appliances having *different teeth-receiving cavity* geometries *based on successive intermediate tooth arrangements, the geometries* selected to progressively reposition the teeth from the first intermediate arrangement to successive intermediate arrangements; and
   a final appliance having a geometry selected to progressively reposition the teeth from [the] *a* last intermediate arrangement to the final tooth arrangement, wherein the appliances comprise polymeric shells having cavities and wherein the *teeth-receiving* cavities of successive shells have different geometries shaped to receive and resiliently reposition teeth from one arrangement to a successive arrangement, *wherein at least one of the successive intermediate tooth arrangements is generated prior to generating a preceding successive intermediate tooth arrangement.*

6. A method for repositioning teeth from an initial tooth arrangement to a final tooth arrangement, said method comprising:
   *providing a set of at least two dental incremental position adjustment appliances having different successive teeth-receiving cavity geometries to a treating professional;*
   *subsequent to the providing step,* placing a first incremental position adjustment appliance *from the set of appliances* in a patient's mouth, wherein the first appliance has a geometry selected to reposition the teeth from the initial tooth arrangement to a first intermediate arrangement;
   successively replacing one or more additional appliances *from the set* in the patient's mouth with the next incremental position adjustment appliance *of the set,* wherein the additional appliances have geometries selected to progressively reposition the teeth from the first intermediate arrangement to successive intermediate arrangements; and
   placing a final appliance into the patient's mouth, wherein the final appliance has a geometry selected to progressively reposition the teeth from [the] *a* last intermediate arrangement to the final tooth arrangement, wherein the appliances comprise polymeric shells having cavities [shaped], and wherein the *teeth-receiving* cavities of successive shells have [difficult] *different* geometries *shaped* to receive and resiliently reposition teeth from one arrangement to a successive arrangement.

12. An improved method for repositioning teeth using appliances comprising polymeric shells having cavities shaped to receive and resiliently reposition teeth to produce a final tooth arrangement, wherein the improvement comprises[determining]*:*
   (*i*) *generating* at the outset of treatment *different teeth-receiving cavity* geometries for at least three appliances which are to be worn successively by a patient to reposition teeth from an initial tooth arrangement to the final tooth arrangement, *wherein the at least three appliances include at least two successive intermediate appliances;*
   (*ii*) wherein the cavities of successive shells have different geometries.

13. An improved method as in claim 12, wherein at least four geometries [determined] *are generated* at the outset.

14. An improved method as in claim 13, wherein at least ten geometries are [determined] *generated* at the outset.

15. An improved method as in claim 14, wherein at least twenty-five geometries are [determined] *generated* at the outset.

17. A system for repositioning teeth from an initial tooth arrangement to a final tooth arrangement, said system comprising a plurality of dental incremental position adjustment appliances including:
   a first appliance having a geometry selected to reposition the teeth from the intial tooth arrangement to a first intermediate arrangement;
   [one or more] *at least three* intermediate appliances having *different teeth-receiving cavity* geometries selected to progressively reposition the teeth from the first intermediate arrangement to successive intermediate arrangements, *wherein at least two target intermediate tooth arrangements are generated prior to generating at least one intermediate tooth arrangement between the target arrangements*; and
   a final appliance having a geometry selected to progressively reposition the teeth from [the] *a* last intermediate arrangement to the final tooth arrangement, wherein the appliances comprise polymeric shells having cavities shaped to receive and resiliently reposition teeth from one arrangement to a successive arrangement and wherein the tooth positions defined by the cavities in each successive appliance differ from those defined by the prior appliance by no more than 2 mm.

21. A method for repositioning teeth from an initial tooth arrangement to a final tooth arrangement, said method comprising:
   *providing a set of at least two dental incremental position adjustment appliances having different successful teeth-receiving cavity geometries;*
   *subsequent to the providing step,* placing a first incremental position adjustment appliance *from the set of appliances* in a patient's mouth, wherein the first appliance has a geometry selected to reposition the teeth from the initial tooth arrangement to a first intermediate arrangement;

successively replacing one or more additional appliances from the set in the patient's mouth with the next incremental position adjustment appliance of the set, wherein the additional appliances have *different teeth-receiving cavity* geometries selected to progressively reposition the teeth from the first intermediate arrangement to successive intermediate arrangements; and placing a final appliance into the patient's mouth, wherein the final appliance has a geometry selected to progressively reposition the teeth from [the] *a* last intermediate arrangement to the final tooth arrangement, wherein the appliances comprise polymeric shells having cavities shaped to receive and resiliently reposition teeth from one arrangement to a successive arrangement, and wherein the tooth positions defined by the cavities in each successive appliance differ from those defined by the prior appliance by no more than 2 mm.

26. An improved method for repositioning teeth using appliances comprising polymeric shells having cavities shaped to receive and resiliently reposition teeth to produce a final tooth arrangement, wherein the improvement comprises[determining]:
  (i) generating at the outset of treatment *different teeth-receiving cavity* geometries for at least three appliances which are to be worn successively by a patient to reposition teeth from an initial tooth arrangement to the final tooth arrangement, *wherein the at least three appliances include at least two successive intermediate appliances;*
  (ii) wherein the tooth positions defined by the cavities in each successive appliance differ from those defined by the previous appliance by no more than 2 mm.

27. An improved method as in claim 26, wherein at least four geometries [determined] *are generated* at the outset.

28. An improved method as in claim 27, wherein at least ten geometries are [determined] *generated* at the outset.

29. An improved method as in claim 28, wherein at least twenty-five geometries are [determined] *generated* at the outset.

30. *A system as in claim 1, wherein at least one of the appliance has a geometry configured to conform to at least one tooth that has been shaved down on one or more surfaces.*

31. *A system as in claim 1, wherein the initial tooth arrangement is generated, the final tooth arrangement is generated, and at least one intermediate tooth arrangement is generated, in that order.*

32. *A system as in claim 31, wherein the at least one intermediate tooth arrangement is generated prior to fabrication of at least one appliance corresponding with a tooth arrangement that precedes the at least one intermediate tooth arrangement.*

33. *A system as in claim 1, wherein each of the tooth positions defined by the cavities in each successive appliance differs from each from those defined by the prior appliance by no more than 0.5 mm.*

34. *A system as in claim 1, wherein the initial tooth arrangement is generated, a subsequent intermediate tooth arrangement is generated, and at least one preceding intermediate tooth arrangement is generated, in that order, prior to fabrication of at least one appliance corresponding with a tooth arrangement that precedes the subsequent intermediate tooth arrangement, and wherein each of the tooth positions defined by the cavities in each successive appliance differs from each of those defined by the prior appliance by no more than 0.5 mm.*

35. *A method as in claim 6, further comprising generating tooth arrangements corresponding to the geometries of the appliances, wherein the tooth arrangement on which the geometry of at least one of the appliances is based is generated prior to generation of the tooth arrangement on which the geometry of a preceding appliance is based.*

36. *A method as in claim 6, further comprising generating tooth arrangements corresponding to the geometries of the appliances, wherein the initial tooth arrangement is generated, the final tooth arrangement is generated, and at least one intermediate tooth arrangement between the two is generated, in that order.*

37. *A method as in claim 36, wherein the at least one intermediate tooth arrangement and at least one additional intermediate tooth arrangement or the final tooth arrangement are generated prior to fabrication of at least one appliance corresponding with a tooth arrangement that precedes the at least one intermediate tooth arrangement.*

38. *A method as in claim 6, wherein each of the tooth positions defined by the cavities in each successive appliance differs from each of those defined by the prior appliance by no more than 0.5 mm.*

39. *A method as in claim 6, further comprising generating tooth arrangements corresponding to the geometries of the appliances, wherein the initial tooth arrangement is generated, a subsequent intermediate tooth arrangement is generated, and at least one preceding intermediate tooth arrangement between the two is generated, in that order, wherein at least one of the intermediate tooth arrangements and at least one additional intermediate tooth arrangement or the final tooth arrangement are generated prior to fabrication of at least one appliance corresponding with a tooth arrangement that precedes the successive intermediate tooth arrangement, and wherein each of the tooth positions defined by the cavities in each successive appliance differs from each of those defined by the prior appliance by no more than 0.5 mm.*

40. *An improved method as in claim 12, wherein generating the geometries of the appliances comprises generating tooth arrangements corresponding to the geometries, and wherein the tooth arrangement on which the geometry of at least one of the appliances is based is generated prior to generation of the tooth arrangement on which the geometry of a preceding appliance is based.*

41. *An improved method as in claim 12, wherein the initial tooth arrangement is generated, the final tooth arrangement is generated, and at least one intermediate tooth arrangement between the two is generated, in that order.*

42. *An improved method as in claim 41, wherein at the least intermediate tooth arrangement and at least one additional intermediate tooth arrangement or the final tooth arrangement are generated prior to fabrication of at least one appliance corresponding with a tooth arrangement that precedes the at least one intermediate tooth arrangement.*

43. *An improved method as in claim 12, further comprising:*
  *providing at least some of the appliances to a treating professional or a patient at the outset of treatment.*

44. *An improved method as in claim 12, wherein each of the tooth positions defined by the cavities in each successive appliance differs from each of those defined by the prior appliance by no more than 0.5 mm.*

45. *An improved method as in claim 12, wherein the initial tooth arrangement is generated, a succeeding intermediate tooth arrangement is generated, and at least one preceding intermediate tooth arrangement between the two is generated, in that order, wherein at least one of the intermediate tooth arrangements and at least one additional intermediate tooth arrangement or the final tooth arrangement* are generated prior to fabrication of at least one appliance having a tooth arrangement that precedes the at least one intermediate tooth arrangement, and wherein each of the tooth positions defined by the cavities in each successive appliance differs from each of those defined by the prior appliance by no more than 0.5 mm.

46. A system as in claim 17, wherein one of the target intermediate tooth arrangements comprises the first intermediate arrangement.

47. A system as in claim 17, wherein the final tooth arrangement comprises a target tooth arrangement, which arrangement is generated prior to generating at least one intermediate tooth arrangement between one of the other target arrangements and the final arrangement.

48. A system as in claim 17, wherein at least one of the target intermediate arrangements is provided by a treating professional via a prescription.

49. A system as in claim 17, wherein at least one of the target intermediate arrangements is specified by a user of a system for generating the arrangements.

50. A system as in claim 17, wherein each of the tooth positions defined by the cavities in each successive appliance differs from each of those defined by the prior appliance by no more than 0.5 mm.

51. A system as in claim 17, wherein the final tooth arrangement comprises a target tooth arrangement, which arrangement is generated prior to generating at least one intermediate tooth arrangement between one of the other target arrangements and the final arrangement, and wherein each of the tooth positions defined by the cavities in each successive appliance differs from each of those defined by the prior appliance by no more than 0.5 mm.

52. An improved method as in claim 26, wherein generating the geometries of the appliances comprises generating tooth arrangements corresponding to the geometries, and wherein the tooth arrangement on which the geometry of at least one of the appliances is based is generated prior to generation of the tooth arrangement on which the geometry of a preceding appliance is based.

53. An improved method as in claim 26, wherein the intial tooth arrangement is generated, the final tooth arrangement is generated, and at least one intermediate tooth arrangement between the two is generated, in that order.

54. An improved method as in claim 53, wherein the at least one intermediate tooth arrangement and at least one additional intermediate tooth arrangement or the final tooth arrangement are generated prior to fabrication of at least one appliance corresponding with a tooth arrangement that precedes the at least one intermediate tooth arrangement.

55. An improved method as in claim 26, further comprising:

provideing at least some of the appliances at the outset of treatment.

56. An improved method as in claim 26, wherein each of the tooth positions defined by the cavities in each successive appliance differs from each of those defined by the prior appliance by no more than 0.5 mm.

57. An improved method as in claim 26, wherein the initial tooth arrangement is generated, a subsequent intermediate tooth arrangement is generated, and at least one preceding intermediate tooth arrangement between the two is generated, in that order, wherein at least one of the intermediate tooth arrangements and at least one additional intermediate tooth arrangement or the final tooth arrangement are generated prior to fabrication of at least one appliance corresponding with a tooth arrangement that precedes the successive intermediate tooth arrangement, and wherein each of the tooth positions defined by the cavities in each successive appliance differs from each of those defined by the prior appliance by no more than 0.5 mm.

58. An improved method for repositioning teeth using appliances comprising polymeric shells having cavities shaped to receive and resiliently reposition teeth to produce a final tooth arrangement, wherein the improvement comprises:

(i) determining and storing at the outset of treatment different teeth-receiving cavity geometries for at least three appliances which are to be worn successively by a patient to reposition teeth from an initial tooth arrangement to the final tooth arrangement, wherein the at least three appliances include at least two successive intermediate appliances;

(ii) wherein the cavities of successive shells have different geometries.

* * * * *